US012624388B2

(12) United States Patent
Campbell et al.

(10) Patent No.: US 12,624,388 B2
(45) Date of Patent: May 12, 2026

(54) METHODS AND KITS FOR DETECTING TAU

(71) Applicants: MESO SCALE TECHNOLOGIES, LLC., Rockville, MD (US); The Henry M. Jackson Foundation For The Advancement Of Military Medicine, Inc., Bethesda, MD (US); The United States of America, as represented by the Secretary, Department of Health and Human Services, Bethesda, MD (US)

(72) Inventors: Christopher Campbell, Columbia, MD (US); Kimbra Kenney, Bethesda, MD (US); Jessica Gill, Reston, VA (US)

(73) Assignees: MESO SCALE TECHNOLOGIES, LLC., Rockville, MN (US); The Henry M. Jackson Foundation For The Advancement Of Military Medicine, Inc., Bethesda, MD (US); The United States of America,as represented by the Secretary,Department of Health and Human Services, Bethesda, MD (US)

( * ) Notice: Subject to any disclaimer, the term of this patent is extended or adjusted under 35 U.S.C. 154(b) by 432 days.

(21) Appl. No.: 17/453,991

(22) Filed: Nov. 8, 2021

(65) Prior Publication Data

US 2022/0145363 A1 May 12, 2022

Related U.S. Application Data

(60) Provisional application No. 63/111,333, filed on Nov. 9, 2020.

(51) Int. Cl.
| | |
|---|---|
| *C12Q 1/686* | (2018.01) |
| *C12Q 1/6853* | (2018.01) |
| *G01N 21/76* | (2006.01) |
| *G01N 27/327* | (2006.01) |

(52) U.S. Cl.
CPC ........... *C12Q 1/686* (2013.01); *C12Q 1/6853* (2013.01); *G01N 21/76* (2013.01); *G01N 27/327* (2013.01); *C12Q 2537/137* (2013.01); *C12Q 2565/531* (2013.01); *C12Q 2600/112* (2013.01); *G01N 2458/10* (2013.01)

(58) Field of Classification Search
CPC .............................. C12Q 1/686; C12Q 1/6853; C12Q 2537/137; C12Q 2565/531; C12Q 2600/112; G01N 21/76; G01N 27/327; G01N 2458/10
See application file for complete search history.

(56) References Cited

U.S. PATENT DOCUMENTS

| | | |
|---|---|---|
| 5,714,089 A | 2/1998 | Bard et al. |
| 6,136,268 A | 10/2000 | Ala-Kleme et al. |
| 6,316,607 B1 | 11/2001 | Massey et al. |
| 6,468,741 B1 | 10/2002 | Massey et al. |
| 6,479,233 B1 | 11/2002 | Bard et al. |
| 6,808,939 B2 | 10/2004 | Sigal et al. |
| 6,977,722 B2 | 12/2005 | Wohlstadter et al. |
| 7,842,246 B2 | 11/2010 | Wohlstadter et al. |
| 9,499,573 B2 | 11/2016 | Bergmann |
| 9,499,858 B2 | 11/2016 | Nadeau et al. |
| 2004/0022677 A1 | 2/2004 | Wohlstadter et al. |
| 2004/0189311 A1 | 9/2004 | Glezer et al. |
| 2005/0052646 A1 | 3/2005 | Wohlstadter et al. |
| 2005/0142033 A1 | 6/2005 | Glezer et al. |
| 2014/0165061 A1 | 6/2014 | Greene et al. |
| 2014/0256588 A1 | 9/2014 | Glezer et al. |
| 2014/0272939 A1 | 9/2014 | Aghvanyan et al. |
| 2014/0274775 A1 | 9/2014 | Glezer et al. |
| 2015/0119273 A1 | 4/2015 | Goldstein et al. |
| 2016/0069872 A1 | 3/2016 | Glezer et al. |
| 2017/0089892 A1 | 3/2017 | Aghvanyan et al. |
| 2017/0089912 A1 | 3/2017 | Alessio et al. |
| 2017/0168047 A1 | 6/2017 | Aghvanyan et al. |

(Continued)

FOREIGN PATENT DOCUMENTS

| | | |
|---|---|---|
| EP | 1473567 A1 | 11/2004 |
| WO | 2014/008404 A1 | 1/2014 |

(Continued)

OTHER PUBLICATIONS

Goedert, M et al. "Cloning and sequencing of the cDNA encoding a core protein of the paired helical filament of Alzheimer disease: identification as the microtubule-associated protein tau." Proceedings of the National Academy of Sciences of the United States of America vol. 85,11: 4051-5. doi:10 (Year: 1988).*

(Continued)

*Primary Examiner* — Ann Montgomery
*Assistant Examiner* — Mckenzie A Dunn
(74) *Attorney, Agent, or Firm* — MEDLER FERRO WOODHOUSE & MILLS PLLC

(57) ABSTRACT

The invention relates to methods and kits for assessing brain injury, e.g., traumatic brain injury resulting from blast exposure. The invention provides methods of quantifying the amount of phosphorylated tau or total tau in a biological sample. The invention further provides a method of determining the number of blast exposures experienced by a subject. Also provided herein are kits for detecting phosphorylated tau or total tau in a biological sample.

20 Claims, 13 Drawing Sheets

Specification includes a Sequence Listing.

(56) References Cited

U.S. PATENT DOCUMENTS

| | | | |
|---|---|---|---|
| 2018/0029034 A1 | 2/2018 | Glezer et al. | |
| 2019/0011441 A1 | 1/2019 | Glezer et al. | |
| 2019/0083976 A1 | 3/2019 | Glezer et al. | |
| 2019/0291103 A1 | 9/2019 | Glezer et al. | |
| 2019/0391140 A1 | 12/2019 | Aghvanyan et al. | |
| 2021/0048431 A1 | 2/2021 | Debad et al. | |
| 2021/0190778 A1 | 6/2021 | Aghvanyan et al. | |
| 2021/0291168 A1 | 9/2021 | Glezer et al. | |
| 2021/0382043 A1 | 12/2021 | Routenberg et al. | |
| 2021/0389304 A1 | 12/2021 | Routenberg | |
| 2021/0402390 A1 | 12/2021 | Glezer et al. | |
| 2022/0099661 A1 | 3/2022 | Kenten et al. | |
| 2022/0145363 A1 | 5/2022 | Campbell et al. | |
| 2022/0357318 A1 | 11/2022 | Aghvanyan et al. | |
| 2023/0349920 A1 | 11/2023 | Routenberg et al. | |
| 2023/0407380 A1 | 12/2023 | Glezer et al. | |
| 2024/0409983 A1 | 12/2024 | Routenberg et al. | |
| 2025/0035615 A1 | 1/2025 | Routenberg | |
| 2025/0244342 A1* | 7/2025 | Stengelin | G01N 33/6896 |

FOREIGN PATENT DOCUMENTS

| | | |
|---|---|---|
| WO | 2019/173703 A1 | 9/2019 |
| WO | 2019/222708 A2 | 11/2019 |
| WO | 2020/086751 A1 | 4/2020 |
| WO | 2020/142313 A1 | 7/2020 |
| WO | 2020/180645 A1 | 9/2020 |
| WO | 2022/006236 A1 | 1/2022 |
| WO | 2022/051481 A2 | 3/2022 |
| WO | 2023/196927 A1 | 10/2023 |
| WO | 2023/212315 A2 | 11/2023 |

OTHER PUBLICATIONS

Alonso et al., "Hyperphosphorylation induces self-assembly of τ into tangles of paired helical filaments/straight filaments," Proc Natl Acad Sci USA 98(12):6923-6928 (2001).

Chen et al., "Learnings about the complexity of extracellular tau aid development of a blood-based screen for Alzheimer's disease," Alzheimers Dement. 15(3):487-496 (2019).

Cleveland et al., "Purification of tau, a microtubule-associated protein that induces assembly of microtubules from purified tubulin," J Mol Biol 116(2):207-225 (1977).

Goldstein et al., "Chronic traumatic encephalopathy in blast-exposed military veterans and a blast neurotrauma mouse model," Sci Transl Med 4(134):134ra60 (2012).

Janelidze et al., "Plasma P-tau181 in Alzheimer's disease: relationship to other biomarkers, differential diagnosis, neuropathology and longitudinal progression to Alzheimer's dementia," Nature Medicine 26(3):379-386 (2020).

Kenney et al., "Higher exosomal phosphorylated tau and total tau among veterans with combat-related repetitive chronic mild traumatic brain injury," Brain Injury 32(10):1276-1284 (2018).

Matsuo et al., "Biopsy-derived adult human brain tau is phosphorylated at many of the same sites as Alzheimer's disease paired helical filament tau," Neuron 13(4):989-1002 (1994).

Mckee et al., "The spectrum of disease in chronic traumatic encephalopathy," Brain 136(1):43-64 (2013).

Omalu et al., "Chronic Traumatic Encephalopathy in a National Football League Player," Neurosurgery 57(1):128-134 (2005).

Papanikolopoulou et al., "*Drosophila* Tau Negatively Regulates Translation and Olfactory Long-Term Memory, But Facilitates Footshock Habituation and Cytoskeletal Homeostasis," J Neurosci 39(42):8315-8329 (2019).

Rubenstein et al., "Comparing Plasma Phospho Tau, Total Tau, and Phospho Tau-Total Tau Ratio as Acute and Chronic Traumatic Brain Injury Biomarkers," JAMA Neurol 74(9):1063-1072 (2017).

Stern et al., "Tau Positron-Emission Tomography in Former National Football League Players," N Engl J Med 380(18):1716-1725 (2019).

Taniguchi et al., "Phosphorylation of Tau Is Regulated by Pkn*," J Biol Chem 276(13):10025-10031 (2001).

Thijssen et al., "Diagnostic value of plasma phosphorylated tau181 in Alzheimer's disease and frontotemporal lobar degeneration," Nat Med 26(3):387-397 (2020).

Wang et al., "Microtubule-associated protein tau in development, degeneration and protection of neurons," Prog Neurobiol 85(2):148-175 (2008).

Dickstein et al., "Brain and Blood Biomarkers of Tauopathy and Neuronal Injury in Humans and Rats with Neurobehavioral Syndromes Following Blast Exposure," Molecular Psychiatry 26(10):5940-5954 (2020).

Hyytiä et al., "A Comparison of Capture Antibody Fragments in Cardiac Troponin I Immunoassay," Clinical Biochemistry 46(12):963-968 (2013).

Lachno et al., "Validation of ELISA Methods for Quantification of Total Tau and Phosporylated-Tau181 in Human Cerebrospinal Fluid with Measurement in Specimens from Two Alzheimer's Disease Studies," Journal of Alzheimer's Disease 26(3):531-541 (2011).

Rubenstein et al., "Comparing Plasma Phospho Tau, Total Tau, and Phospho Tau-Total Tau Ratio as Acute and Chronic Traumatic Brain Injury Biomarkers," 74(9):1063-1072 (2017).

Yamamoto et al., "Impact & Blast Traumatic Brain Injury: Implications for Therapy," Molecules 23(2):1-11 (2018).

International Search Report issued in PCT/US2021/072289, mailed Feb. 16, 2022.

Athar et al., "Recent advances on drug development and emerging therapeutic agents for Alzheimer's disease," Molecular Biology Reports 48(7):5629-5645 (2021).

Ballatore et al., "Tau-mediated neurodegeneration in Alzheimer's disease and related disorders," *Nature Reviews Neuroscience* 8(9):663-672 (2007).

Brickman et al., "Plasma p-tau181, p-tau217, and other blood-based Alzheimer's disease biomarkers in a multi-ethnic, community study," Alzheimer's & Dementia : The Journal of the Alzheimer's Association 17(8):1353-1364 (2021).

Dixon et al., "Cognitively Elite, Cognitively Normal, and Cognitively Impaired Aging: Neurocognitive Status and Stability Moderate Memory Performance," J Clin Exp Neuropsychol 36(4):418-430 (2014).

Dougal et al., "Effect of Transcranial Near-Infrared Light 1068 nm Upon Memory Performance in Aging Healthy Individuals: A Pilot Study," Photomodulation, Photomedicine, and Laser Surgery 39(10):654-660 (2021).

Fisher, "Big Tau: What We Know, and We Need to Know," eNeuro 10(5) (2023).

Gonzalez-Ortiz et al., "Brain-derived tau: a novel blood-based biomarker for Alzheimer's disease-type neurodegeneration," Brain 146:1152-1165 (2023).

International Search Report and Written Opinion in PCT/US2025/033639, dated Sep. 17, 2025.

International Search Report, International Application No. PCT/US2023/065471, Mailing Date: Aug. 14, 2023.

Karikari et al., "Blood phosphorylated tau 181 as a biomarker for Alzheimer's disease: a diagnostic performance and prediction mode Iii ng study using data from four prospective cohorts," The Lancet Neurology 19(5):422-433 (2020).

Kent et al., "Sleep and its Regulation: An Emerging Pathogenic and Treatment Frontier in Alzheimer's disease," Progress in Neurobiology 197:101902 (2021).

Kivisäkk et al., "Clinical evaluation of a novel plasma pTau217 electrochemiluminescence immunoassay in Alzheimer's disease," Nature Scientific Reports 14:629 (2024).

Lovestone et al., "The phosphorylation of tau: a critical stage in neurodevelopment and neurodegenerative processes," *Neurosciences* 78(2):309-324 (1997).

Meredith Jr. et al., "Characterization of Novel CSF Tau and ptau Biomarkers for Alzheimer's Disease," PLoS ONE 8(10): e76523 (2013).

Mitchell, "Is it time to separate subjective cognitive complaints from the diagnosis of mild cognitive impairment?," Age Ageing 37(5):497-499 (2008).

(56)  References Cited

OTHER PUBLICATIONS

Neugroschl et al., "Alzheimer's disease: diagnosis and treatment across the spectrum of disease severity," Mt Sinai J Med. 78(4): 596-612 (2011).

Petersen et al., "Mild cognitive impairment: clinical characterization and outcome," Arch Neurol 56:303-308 (1999).

Rodriguez et al., "Plasma p-tau181 accurately predicts Alzheimer's disease pathology at least 8 years prior to post mortem and improves the clinical characterisation of cognitive decline," Acta Neuropathologica 140(3):267-278 (2020).

Spencer et al., "Immunotherapy for Alzheimer's disease: past, present and future," Frontiers in Aging Neuroscience, 6:114 (2014).

Thijssen et al., "Association of Plasma P-tau217 and P-tau181 with clinical phenotype, neuropathology, and imaging markers in Alzheimer's disease and frontotemporal lobar degeneration: a retrospective diagnostic performance study," Lancet Neurol. 20(9):739-752 (2021).

Yu et al., "Plasma p-tau181 and p-tau217 in discriminating Part, Ad and other key neuropathologies in older adults," Acta Neuropathol (Berl) 146(1):1-11 (2023).

Zhang et al., "The emerging role of exosomes in Alzheimer's disease," Ageing Research Reviews 68:101321 (2021).

* cited by examiner

Neurodegeneration

- Aβ38
- Aβ40
- Aβ42
- APP
- α-synuclein
- DJ-1/PARK7
- NF-H
- NF-L*
- Total tau*

- Phospho tau
  Site specific

| | |
  |---|---|
  | T181* | trans T231* |
  | T175* | S396* |
  | S214* | S610* |
  | cis T231* | |

Microvascular Dysfunction

Angiogenesis

- Ang-1
- Ang-2
- bFGF
- Flt-1
- PlGF
- Tie-2
- VEGF
- VEGF-C
- VEGF-D

Vascular Injury

- CRP
- E-selectin
- ICAM-1
- ICAM-3
- PDGFRβ
- P-selectin
- SAA
- Thrombomodulin
- VCAM-1
- VWF

Neuroinflammation

- Eotaxin
- GM-CSF
- IFN-γ*
- IL-1α
- IL-1β
- IL-2*
- IL-4
- IL-5
- IL-6*
- IL-7
- IL-8
- IL-10*
- IL-12/
- IL-23p40
- IL-13
- IL-15
- IL-16
- IL-17A
- IL-21
- IL-22*
- IL-23*
- IL-25*
- IP-10
- MCP-1
- MCP-4
- MDC
- NPTX1
- TARC
- TNF-α*
- TNF-β

Glial

- GFAP*
- IL-17
- S100B
- YKL-40

FIG. 1

| Biomarker | Odds Ratio | p value |
|---|---|---|
| S396_ratio | 10.435 | 0.005 |
| cis_T231_ratio | 9.553 | 0.005 |
| p.tau.S293 | 7.232 | 0.006 |
| IL12.p70 | 13.018 | 0.007 |
| S293_ratio | 6.057 | 0.010 |
| p.tau.S396 | 4.936 | 0.014 |
| p.tau.cis.T231 | 4.999 | 0.015 |
| p.tau.S214 | 9.541 | 0.016 |
| p.tau.T175 | 3.437 | 0.032 |
| T175_ratio | 3.654 | 0.032 |
| GFAP | 0.158 | 0.050 |
| S214_ratio | 4.692 | 0.066 |
| IL.8 | 8.126 | 0.071 |
| p.tau.trans.T231 | 5.455 | 0.085 |
| MCP.1 | 5.480 | 0.090 |
| p.tau.T181 | 3.263 | 0.106 |
| T181_ratio | 3.588 | 0.114 |
| VEGF.D | 0.158 | 0.149 |
| SAA | 0.496 | 0.156 |
| Thrombomodulin | 19.583 | 0.171 |
| Eotaxin | 4.498 | 0.179 |
| S100beta | 0.268 | 0.180 |
| TSLP | 3.250 | 0.187 |
| P.selectin | 0.239 | 0.207 |
| MDC | 4.406 | 0.248 |
| bFGF | 0.514 | 0.253 |
| PlGF | 7.658 | 0.260 |
| TNF.alpha | 4.619 | 0.262 |

| Biomarker | Odds Ratio | p value |
|---|---|---|
| E.Selectin | 2.794 | 0.285 |
| trans_T231_ratio | 2.104 | 0.308 |
| CRP | 0.730 | 0.338 |
| IL17A | 1.625 | 0.358 |
| VEGFC | 0.367 | 0.404 |
| MIP.1alpha | 3.253 | 0.446 |
| IP10 | 1.665 | 0.493 |
| TARC | 1.589 | 0.494 |
| NF.L | 1.824 | 0.506 |
| PDGFRbeta | 1.488 | 0.542 |
| IL.2 | 0.540 | 0.557 |
| IL.6 | 0.709 | 0.594 |
| IL.22 | 0.768 | 0.635 |
| Eotaxin.3 | 1.374 | 0.647 |
| Flt.1 | 0.473 | 0.663 |
| VCAM.1 | 1.890 | 0.739 |
| MCP.4 | 0.726 | 0.746 |
| ICAM.3 | 0.679 | 0.814 |
| IL.13 | 0.723 | 0.818 |
| Tau | 1.175 | 0.830 |
| DJ.1 | 1.171 | 0.854 |
| IL.4 | 0.675 | 0.858 |
| IL.10 | 0.883 | 0.858 |
| VEGF | 1.105 | 0.861 |
| Tie.2 | 0.886 | 0.950 |
| IFN.gamma | 0.976 | 0.969 |
| MIP.1beta | 1.024 | 0.982 |
| ICAM.1 | 0.968 | 0.985 |

FIG. 2A

| Biomarker | Odds Ratio | p value |
|---|---|---|
| p.tau.S293 | 5.288 | 0.006 |
| p.tau.T181 | 5.579 | 0.008 |
| p.tau.S396 | 4.201 | 0.011 |
| p.tau.cis.T231 | 3.790 | 0.016 |
| p.tau.S214 | 6.426 | 0.030 |
| IL10 | 0.280 | 0.051 |
| S396_ratio | 3.888 | 0.071 |
| p.tau.T175 | 2.386 | 0.076 |
| IL12.p70 | 5.043 | 0.085 |
| cis_T231_ratio | 3.452 | 0.089 |
| p.tau.trans.T231 | 4.608 | 0.095 |
| GFAP | 0.240 | 0.108 |
| Flt.1 | 0.092 | 0.117 |
| S293_ratio | 2.648 | 0.120 |
| T181_ratio | 3.157 | 0.127 |
| Tau | 2.532 | 0.160 |
| VEGF.C | 0.235 | 0.166 |
| IL8 | 3.530 | 0.194 |
| Thrombomodulin | 11.581 | 0.201 |
| MDC | 4.058 | 0.213 |
| DJ.1 | 2.295 | 0.264 |
| NF.L | 2.464 | 0.264 |
| IFN.gamma | 0.550 | 0.272 |
| IL13 | 0.312 | 0.334 |
| Eotaxin.3 | 0.556 | 0.337 |
| MCP.4 | 0.444 | 0.343 |
| T175_ratio | 1.604 | 0.400 |
| IL2 | 0.457 | 0.407 |
| TNF.alpha | 0.394 | 0.413 |
| S100beta | 0.494 | 0.420 |

| Biomarker | Odds Ratio | p value |
|---|---|---|
| bFGF | 0.672 | 0.422 |
| Tie.2 | 0.314 | 0.501 |
| PDGFRbeta | 0.702 | 0.510 |
| TSLP | 1.665 | 0.516 |
| IL22 | 0.735 | 0.532 |
| MCP.1 | 0.630 | 0.595 |
| E.Selectin | 1.551 | 0.596 |
| IL.4 | 0.472 | 0.704 |
| IP.10 | 0.810 | 0.754 |
| ICAM.3 | 1.571 | 0.758 |
| PlGF | 1.611 | 0.761 |
| S214_ratio | 1.249 | 0.775 |
| VEGF.D | 0.733 | 0.778 |
| P.selectin | 0.786 | 0.809 |
| Eotaxin | 1.247 | 0.810 |
| VEGF | 0.898 | 0.826 |
| trans_T231_ratio | 0.874 | 0.840 |
| IL.6 | 0.895 | 0.841 |
| ICAM.1 | 1.340 | 0.852 |
| VCAM.1 | 1.355 | 0.862 |
| IL.17A | 1.084 | 0.883 |
| MIP.1alpha | 0.806 | 0.887 |
| TARC | 1.083 | 0.889 |
| SAA | 1.049 | 0.910 |
| CRP | 0.969 | 0.911 |
| MIP.1beta | 1.016 | 0.986 |

FIG. 4

| Biomarker | Mann-Whitney P-Value | AUC | Subjects with ≥ 2 Blast TBIs | Subjects with 0-1 Blast TBI | Geometric Mean of Subjects with ≥ 2 Blast TBIs | Geometric Mean of Subjects with 0-1 Blast TBI | Ratio of Geometric Means |
|---|---|---|---|---|---|---|---|
| S293_ratio | 0.002 | 0.73 | 17 | 113 | 0.0309 | 0.0202 | 1.5 |
| S396_ratio | 0.002 | 0.73 | 17 | 113 | 0.0726 | 0.0498 | 1.5 |
| p.tau.S214 | 0.003 | 0.75 | 17 | 113 | 67.3 | 46.6 | 1.4 |
| p.tau.S293 | 0.003 | 0.72 | 17 | 113 | 104 | 58.9 | 1.8 |
| p.tau.S396 | 0.009 | 0.70 | 17 | 113 | 244 | 145 | 1.7 |
| T175_ratio | 0.010 | 0.69 | 17 | 113 | 0.0523 | 0.035 | 1.5 |
| p.tau.T175 | 0.011 | 0.69 | 17 | 113 | 175 | 102 | 1.7 |
| IL12.p70 | 0.021 | 0.75 | 17 | 113 | 0.0826 | 0.0753 | 1.1 |
| S214_ratio | 0.042 | 0.65 | 17 | 113 | 0.02 | 0.016 | 1.3 |
| p.tau.trans.T231 | 0.049 | 0.74 | 17 | 113 | 147 | 113 | 1.3 |
| VEGF.C | 0.053 | 0.35 | 17 | 113 | 159 | 181 | 0.9 |
| cis_T231_ratio | 0.058 | 0.64 | 17 | 113 | 0.126 | 0.096 | 1.3 |
| p.tau.cis.T231 | 0.068 | 0.64 | 17 | 113 | 423 | 279 | 1.5 |
| E.Selectin | 0.077 | 0.63 | 17 | 113 | 3,470 | 2,690 | 1.3 |
| p.tau.T181 | 0.105 | 0.62 | 17 | 113 | 33.8 | 24.1 | 1.4 |
| MCP4 | 0.111 | 0.38 | 17 | 113 | 14.5 | 16.9 | 0.9 |
| T181_ratio | 0.114 | 0.62 | 17 | 113 | 0.0101 | 0.0083 | 1.2 |
| Thrombomodulin | 0.156 | 0.61 | 17 | 113 | 2,740 | 2,390 | 1.1 |
| P.selectin | 0.161 | 0.39 | 17 | 113 | 31,100 | 32,200 | 1.0 |
| trans_T231_ratio | 0.197 | 0.60 | 17 | 113 | 0.0439 | 0.039 | 1.1 |
| VEGF.D | 0.238 | 0.41 | 17 | 113 | 187 | 211 | 0.9 |
| IL.2 | 0.249 | 0.59 | 17 | 113 | 93.2 | 81.4 | 1.1 |
| Eotaxin | 0.250 | 0.41 | 17 | 113 | 30.9 | 32.7 | 0.9 |
| Eotaxin.3 | 0.263 | 0.53 | 17 | 113 | 4.05 | 4.16 | 1.0 |

FIG. 6A

| Biomarker | Mann-Whitney P-Value | AUC | Subjects with ≥ 2 Blast TBIs | Subjects with 0-1 Blast TBI | Geometric Mean of Subjects with ≥ 2 Blast TBIs | Geometric Mean of Subjects with 0-1 Blast TBI | Ratio of Geometric Means |
|---|---|---|---|---|---|---|---|
| TARC | 0.304 | 0.42 | 17 | 113 | 45.7 | 48.5 | 0.9 |
| MCP.1 | 0.351 | 0.57 | 17 | 113 | 58.8 | 52 | 1.1 |
| TSLP | 0.358 | 0.57 | 17 | 113 | 26,900 | 22,900 | 1.2 |
| PlGF | 0.379 | 0.57 | 17 | 113 | 3.15 | 2.93 | 1.1 |
| GFAP | 0.382 | 0.43 | 17 | 113 | 48,700 | 56,700 | 0.9 |
| VEGF | 0.388 | 0.43 | 17 | 113 | 169 | 192 | 0.9 |
| VCAM.1 | 0.392 | 0.56 | 17 | 113 | 18,100 | 16,200 | 1.1 |
| MIP.1beta | 0.431 | 0.56 | 17 | 113 | 17.1 | 16.1 | 1.1 |
| S100beta | 0.471 | 0.45 | 17 | 113 | 1,700 | 1,620 | 1.0 |
| IL.10 | 0.477 | 0.45 | 17 | 113 | 358 | 386 | 0.9 |
| PDGFRbeta | 0.490 | 0.55 | 17 | 113 | 60,900 | 50,700 | 1.2 |
| NF.L | 0.530 | 0.55 | 17 | 113 | 29.4 | 26.4 | 1.1 |
| Tau | 0.534 | 0.55 | 17 | 113 | 3,360 | 2,910 | 1.2 |
| Tie.2 | 0.567 | 0.46 | 17 | 113 | 3,700 | 3,500 | 1.6 |
| DJ.1 | 0.576 | 0.54 | 17 | 113 | 863 | 752 | 1.1 |
| IFN.gamma | 0.581 | 0.54 | 17 | 113 | 306 | 290 | 1.1 |
| IL.4 | 0.601 | 0.90 | 17 | 113 | 0.0202 | 0.0217 | 0 |
| IP.10 | 0.629 | 0.54 | 17 | 113 | 72.3 | 68.5 | 1.1 |
| bFGF | 0.639 | 0.46 | 17 | 113 | 1.43 | 1.48 | 1.0 |
| IL.6 | 0.644 | 0.46 | 17 | 113 | 1,660 | 1,650 | 1.0 |
| SAA | 0.649 | 0.53 | 17 | 113 | 255,000 | 211,000 | 1.2 |
| IL.8 | 0.689 | 0.53 | 17 | 113 | 4.34 | 4.15 | 1.0 |
| Flt.1 | 0.725 | 0.53 | 17 | 113 | 60.5 | 58.4 | 1.0 |
| IL.13 | 0.733 | 0.83 | 17 | 113 | 0.377 | 0.392 | 1.0 |
| ICAM.1 | 0.746 | 0.48 | 17 | 113 | 17,200 | 16,200 | 1.1 |
| TNF.alpha | 0.753 | 0.48 | 17 | 113 | 3,730 | 3,490 | 1.1 |
| MDC | 0.772 | 0.52 | 17 | 113 | 246 | 229 | 1.1 |
| MIP.1alpha | 0.773 | 0.71 | 17 | 113 | 3.17 | 3.24 | 1.0 |
| IL.17A | 0.778 | 0.81 | 17 | 113 | 2 | 2.22 | 0.9 |
| ICAM.3 | 0.860 | 0.51 | 17 | 113 | 290 | 280 | 1.0 |
| IL.22 | 0.923 | 0.49 | 17 | 113 | 631 | 612 | 1.0 |
| CRP | 0.956 | 0.50 | 17 | 113 | 113,000 | 100,000 | 1.1 |

FIG. 6B

| Captures: | Capture Antibody 1 | | | | | | Dual Capture Antibodies | | | | Capture Antibody 2 | |
|---|---|---|---|---|---|---|---|---|---|---|---|---|
| | 1 | 2 | 3 | 4 | 5 | 6 | 7 | 8 | 9 | 10 | 11 | 12 |
| A | Cal 01 | Cal 01 | Normal Plasma 1 | Cal 01 | Cal 01 | Normal Plasma 1 | Cal 01 | Cal 01 | Normal Plasma 1 | Cal 01 | Cal 01 | Normal Plasma 1 |
| B | Cal 02 | Cal 02 | Normal Plasma 2 | Cal 02 | Cal 02 | Normal Plasma 2 | Cal 02 | Cal 02 | Normal Plasma 2 | Cal 02 | Cal 02 | Normal Plasma 2 |
| C | Cal 03 | Cal 03 | sTBI Plasma 1 | Cal 03 | Cal 03 | sTBI Plasma 1 | Cal 03 | Cal 03 | sTBI Plasma 1 | Cal 03 | Cal 03 | sTBI Plasma 1 |
| D | Cal 04 | Cal 04 | sTBI Plasma 2 | Cal 04 | Cal 04 | sTBI Plasma 2 | Cal 04 | Cal 04 | sTBI Plasma 2 | Cal 04 | Cal 04 | sTBI Plasma 2 |
| E | Cal 05 | Cal 05 | sTBI CSF 01 | Cal 05 | Cal 05 | sTBI CSF 01 | Cal 05 | Cal 05 | sTBI CSF 01 | Cal 05 | Cal 05 | sTBI CSF 01 |
| F | Cal 06 | Cal 06 | sTBI CSF 02 | Cal 06 | Cal 06 | sTBI CSF 02 | Cal 06 | Cal 06 | sTBI CSF 02 | Cal 06 | Cal 06 | sTBI CSF 02 |
| G | Cal 07 | Cal 07 | Normal CSF 01 | Cal 07 | Cal 07 | Normal CSF 01 | Cal 07 | Cal 07 | Normal CSF 01 | Cal 07 | Cal 07 | Normal CSF 01 |
| H | Cal 08 | Cal 08 | Normal CSF 02 | Cal 08 | Cal 08 | Normal CSF 02 | Cal 08 | Cal 08 | Normal CSF 02 | Cal 08 | Cal 08 | Normal CSF 02 |
| Detects: | Detection Antibody 1 | | | | | | Detection Antibody 2 | | | | | |

FIG. 7

| Sample | Dual Capture Antibodies | Capture Antibody 1 | | Capture Antibody 2 |
|---|---|---|---|---|
| | Detection Antibody 2 | Detection Antibody 1 | Detection Antibody 2 | Detection Antibody 2 |
| Cal 01 - 25,000 pg/mL | 736,965 | 12,456 | 30,651 | 19,973 |
| Cal 02 - 6,250 pg/mL | 241,505 | 2,386 | 6,188 | 4,522 |
| Cal 03 - 1,562 pg/mL | 74,125 | 588 | 1,515 | 1,161 |
| Cal 04 - 391 pg/mL | 18,550 | 212 | 407 | 327 |
| Cal 05 - 98 pg/mL | 4,994 | 112 | 162 | 128 |
| Cal 06 - 24 pg/mL | 1,351 | 86 | 93 | 83 |
| Cal 07 - 6 pg/mL | 399 | 81 | 75 | 68 |
| Cal 08 - 0 pg/mL | 66 | 81 | 65 | 61 |
| Hill Slope | 0.97 | 1.11 | 1.06 | 1.03 |
| Estimated LOD | 0.4 | 99 | 32 | 39 |
| Normal Plasma 1 | 133 | 83 | 81 | 62 |
| Normal Plasma 2 | 1,141 | 91 | 91 | 96 |
| Pooled sTBI Plasma 1 | 22,998 | 87 | 122 | 163 |
| COMA TBI Plasma 2 | 20,598 | 83 | 124 | 239 |
| Normal CSF 01 | 8,658 | 95 | 86 | 93 |
| Normal CSF 02 | 870 | 77 | 73 | 67 |
| TBI CSF 01 | 50,748 | 139 | 328 | 342 |
| TBI CSF 02 | 23,187 | 113 | 134 | 148 |

FIG. 8A

| Platform | Area Under Curve for TBI vs. Uninjured | Area Under Curve for Normal CT vs. Abnormal CT |
|---|---|---|
| SIMOA assay | 0.59 (0.45-0.74) | 0.52 (0.34-0.70) |
| Nucleic acid probe detection assay | 0.83 (0.73-0.94) | 0.74 (0.58-0.90) |

Nucleic acid probe detection assay: TBI vs. Uninjured
Area 0.8342

SIMOA assay: TBI vs. Uninjured
Area 0.5920

Nucleic acid probe detection assay: Abnormal vs Normal CT
Area 0.7385

SIMOA assay: Abnormal vs Normal CT
Area 0.5179

SEQUENCE LISTING

<160> NUMBER OF SEQ ID NOS: 1

<210> SEQ ID NO 1
<211> LENGTH: 441
<212> TYPE: PRT
<213> ORGANISM: Homo sapiens

<400> SEQUENCE: 1

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
        130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
        210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
        290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365
```

-continued

```
Lys Lys Ile Glu Thr His Lys Leu Thr Phe Arg Glu Asn Ala Lys Ala
    370             375             380

Lys Thr Asp His Gly Ala Glu Ile Val Tyr Lys Ser Pro Val Val Ser
385             390             395             400

Gly Asp Thr Ser Pro Arg His Leu Ser Asn Val Ser Ser Thr Gly Ser
                405             410             415

Ile Asp Met Val Asp Ser Pro Gln Leu Ala Thr Leu Ala Asp Glu Val
                420             425             430

Ser Ala Ser Leu Ala Lys Gln Gly Leu
        435             440
```

METHODS AND KITS FOR DETECTING TAU

GOVERNMENT LICENSE RIGHTS

This invention was made with government support under award number W81XWH-17-1-0648 awarded by the United States Department of Defense. The government has certain rights in the invention.

SEQUENCE LISTING

The instant application contains a Sequence Listing which has been submitted electronically in ASCII format and is hereby incorporated by reference in its entirety. Said ASCII copy, created on Jan. 6, 2022, is named 0076-0030US1_SL.txt and is 4,305 bytes in size.

FIELD OF THE INVENTION

The invention relates to methods and kits for assessing brain injury, e.g., traumatic brain injury resulting from blast exposure. The invention provides methods of quantifying the amount of tau, e.g., phosphorylated tau and total tau in a biological sample. The invention further provides a method of determining the number of blast exposures experienced by a subject. Also provided herein are kits for detecting tau, e.g., phosphorylated tau and total tau in a biological sample.

BACKGROUND

Traumatic brain injury (TBI), specifically repeated blast exposures, can cause life-long symptoms in some individuals. Military personnel are particularly susceptible to TBI. In the most severe cases, individuals can develop chronic traumatic encephalopathy (CTE), which is progressive neurodegeneration similar to Alzheimer's disease. Currently, it is difficult to assess an individual's likelihood of developing CTE and to monitor the rate of progression in living donors. Since symptoms of CTE are non-specific, assessments of neurologic and cognitive function may be confounded by other conditions.

A method of assessing risk for neurodegeneration and monitoring rate of neurodegeneration would be valuable for clinical trials of experimental treatments to halt neurodegeneration after TBI. Such methods would aid in enriching clinical trials with suitable participants and as a proximal indicator of efficacy.

SUMMARY OF THE INVENTION

In embodiments, the invention provides a method of quantifying the amount of phosphorylated tau (p-tau) in a biological sample, comprising: (a) contacting the biological sample with: (i) a first capture reagent that binds non-phosphorylated tau; (ii) a second capture reagent that binds non-phosphorylated tau, wherein the first and second capture reagents are on a surface, and the surface further comprises an anchoring reagent; (iii) a first detection reagent that binds non-phosphorylated tau, wherein the first detection reagent comprises a first nucleic acid probe; and (iv) a second detection reagent that binds p-tau, wherein the second detection reagent comprises a second nucleic acid probe, thereby forming a complex on the surface comprising the first and second capture reagents, p-tau, and the first and second detection reagents; (b) using an extension process that requires the first and second nucleic acid probes to be in proximity, extending the second nucleic acid probe to form an extended sequence comprising an anchoring region that binds to the anchoring reagent; (c) binding the extended sequence to the anchoring reagent; and (d) measuring the amount of extended sequence bound to the surface, thereby quantifying the amount of p-tau.

In embodiments, the invention provides a method of quantifying the amount of phosphorylated tau (p-tau) in a biological sample, comprising: (a) contacting the biological sample with: (i) a first capture reagent that binds non-phosphorylated tau; (ii) a second capture reagent that binds non-phosphorylated tau, wherein the first and second capture reagents are on a surface, and the surface further comprises an anchoring reagent; (iii) a detection reagent that binds p-tau, wherein the detection reagent comprises a nucleic acid probe, thereby forming a complex on the surface comprising the first and second capture reagents, p-tau, and the detection reagent; (b) extending the nucleic acid probe to form an extended sequence comprising an anchoring region that binds to the anchoring reagent; (c) binding the extended sequence to the anchoring reagent; and (d) measuring the amount of extended sequence bound to the surface, thereby quantifying the amount of p-tau.

In embodiments, the invention provides a method of quantifying the amount of phosphorylated tau (p-tau) in a biological sample, comprising: (a) contacting the biological sample with: (i) a first capture reagent that binds non-phosphorylated tau; (ii) a second capture reagent that binds non-phosphorylated tau, wherein the first and second capture reagents are on a surface; (iii) a detection reagent that binds p-tau, wherein the detection reagent comprises a detectable label, thereby forming a complex on the surface comprising the first and second capture reagents, p-tau, and the detection reagent; and (c) measuring the amount of detectable label on the surface, thereby quantifying the amount of p-tau.

In embodiments, the invention provides a method of quantifying the amount of total tau (t-tau) in a biological sample, comprising: (a) contacting the biological sample with: (i) a first capture reagent that binds tau; (ii) a second capture reagent that binds tau, wherein the first and second capture reagents are on a surface, and the surface further comprises an anchoring reagent; (iii) a first detection reagent that binds tau, wherein the first detection reagent comprises a first nucleic acid probe; and (iv) a second detection reagent that binds tau, wherein the second detection reagent comprises a second nucleic acid probe, thereby forming a complex on the surface comprising the first and second capture reagents, tau, and the first and second detection reagents; (b) using an extension process that requires the first and second nucleic acid probes to be in proximity, extending the second nucleic acid probe to form an extended sequence comprising an anchoring region that binds to the anchoring reagent; (b) binding the extended sequence to the anchoring reagent; and (c) measuring the amount of extended sequence bound to the surface, thereby quantifying the amount of t-tau. In embodiments, the first and second capture reagents and the first and second detection reagents are capable of binding to phosphorylated and non-phosphorylated tau.

In embodiments, the invention provides a method of quantifying the amount of total tau (t-tau) in a biological sample, comprising: (a) contacting the biological sample with: (i) a first capture reagent that binds tau; (ii) a second capture reagent that binds tau, wherein the first and second capture reagents are on a surface, and the surface further comprises an anchoring reagent; (iii) a detection reagent that binds tau, wherein the detection reagent comprises a nucleic acid probe, thereby forming a complex on the surface comprising the first and second capture reagents, tau, and the detection reagent; (b) extending the nucleic acid probe to form an extended sequence comprising an anchoring region that binds to the anchoring reagent; (c) binding the extended sequence to the anchoring reagent; and (d) measuring the amount of extended sequence bound to the surface, thereby quantifying the amount of t-tau. In embodiments, the first and second capture reagents and the detection reagent are capable of binding to phosphorylated and non-phosphorylated tau.

In embodiments, the invention provides a method of quantifying the amount of total tau (t-tau) in a biological sample, comprising: (a) contacting the biological sample with: (i) a first capture reagent that binds tau; (ii) a second capture reagent that binds tau, wherein the first and second capture reagents are on a surface; (iii) a detection reagent that binds tau, wherein the detection reagent comprises a detectable label, thereby forming a complex on the surface comprising the first and second capture reagents, tau, and the detection reagent; and measuring the amount of detectable label on the surface, thereby quantifying the amount of tau. In embodiments, the first and second capture reagents and the detection reagent are capable of binding to phosphorylated and non-phosphorylated tau.

In embodiments, the invention provides a method of determining the number of blast exposures experienced by a subject, comprising: (a) conducting the method provided herein on a biological sample of the subject to quantify the amount of p-tau in the biological sample; and (b) determining the number of blast exposures experienced by the subject based on the amount of p-tau.

In embodiments, the invention provides a kit for detecting phosphorylated tau (p-tau) in a biological sample comprising, in one or more vials, containers, or compartments: (a) optionally a surface; (b) a first capture reagent that binds non-phosphorylated tau; (c) a second capture reagent that binds non-phosphorylated tau; (d) a first detection reagent that binds non-phosphorylated tau; and (e) a second detection reagent that binds p-tau.

In embodiments, the invention provides a kit for detecting phosphorylated tau (p-tau) in a biological sample comprising, in one or more vials, containers, or compartments: (a) optionally a surface; (b) a first capture reagent that binds non-phosphorylated tau; (c) a second capture reagent that binds non-phosphorylated tau; and (d) a detection reagent that binds p-tau.

In embodiments, the invention provides a kit for detecting total tau (t-tau) in a biological sample comprising, in one or more vials, containers, or compartments: (a) optionally a surface; (b) a first capture reagent that binds tau; (c) a second capture reagent that binds tau; (d) a first detection reagent that binds tau; and (e) a second detection reagent that binds tau. In embodiments, the first and second capture reagents and the first and second detection reagents are capable of binding to phosphorylated and non-phosphorylated tau.

In embodiments, the invention provides a kit for detecting total tau (t-tau) in a biological sample comprising, in one or more vials, containers, or compartments: (a) optionally a surface; (b) a first capture reagent that binds tau; (c) a second capture reagent that binds tau; and (d) a detection reagent that binds tau. In embodiments, the detection reagent comprises a nucleic acid probe. In embodiments, the detection reagent comprises a detectable label. In embodiments, the first and second capture reagents and the detection reagent are capable of binding to phosphorylated and non-phosphorylated tau.

BRIEF DESCRIPTION OF THE DRAWINGS

The following drawings form part of the present specification and are included to further demonstrate exemplary embodiments of certain aspects of the present invention.

FIGS. 1-6B relate to Example 1. FIG. 1 shows a list of biomarkers associated with four key traumatic brain injury (TBI) pathways: neurodegeneration, microvascular dysfunction, gliosis, and neuroinflammation. The biomarkers in bold were analyzed in Example 1.

FIG. 2A shows the results of an ordinal logistic regression calculation between biomarker values and number of blast TBIs. P-tau levels were normalized to total tau levels (e.g., S396 ratio=pS396-tau/tau). Biomarker data were log-transformed (base 10), and log normality was confirmed by a QQ plot. The analysis package computed Odds Ratio (OR) and associated p-value. The OR quantitates the increase in likelihood for another blast TBI for a 10× increase in biomarker level. As described in Example 1, the top biomarkers most closely associated with blast exposure were phosphorylated tau (S396, cis T231, 5293, 5214, T175).

FIG. 3 shows a box plot of pS293-tau levels with subjects grouped by number of blast TBIs (x-axis). The y-axis shows the pS293-tau levels after log transformation (base 10) as described in embodiments herein.

FIG. 4 shows the results of an ordinal logistic regression calculation between biomarker values and total number of TBIs (from blast- and non-blast related events). As described in Example 1, the serum levels of p-tau were correlated with the total number of TBIs, but the correlations were weaker than for blast TBI alone.

FIG. 5 shows a box plot of pS293-tau levels with subjects grouped by number of total TBIs (x-axis). The y-axis shows the pS293-tau levels after log transformation (base 10) as described in embodiments herein.

FIGS. 6A and 6B show the results of a receiver-operator curve (ROC) analysis to assess the differences in biomarkers between subjects with or without repeated TBI. As described in Example 1, p-tau levels were higher in individuals with repeated blast TBI.

FIGS. 7-8B relate to Example 2. FIG. 7 shows an assay plate layout that tests four different tau immunoassay formats as described in Example 2: (1) capture antibody 1 with detection antibody 1; (2) capture antibody 1 with detection antibody 2; (3) dual-capture antibodies with detection antibody 2; and (4) capture antibody 4 with detection antibody 4.

FIGS. 8A and 8B show the results of the immunoassays tested in Example 2. The immunoassay utilizing dual-capture antibodies had a much lower limit of detection compared with immunoassays utilizing a single capture antibody.

FIG. 9A shows the correlation of results obtained from a dual-capture assay with a detection reagent linked to a nucleic acid probe and a dual-capture assay utilizing a detection reagent linked to a detectable label, as described in embodiments herein. FIG. 9B shows the correlation of results obtained from a dual-capture assay utilizing a detection reagent linked to a nucleic acid probe, as described in embodiments herein, and a non-dual capture assay.

FIG. 10A shows the results of a dual-capture assay, as described in embodiments herein, for distinguishing between subjects with TBI or uninjured control subjects. FIG. 10B shows the results of a non-dual capture assay for distinguishing between subjects with TBI or uninjured control subjects. FIG. 10C shows the results of a dual-capture assay, as described in embodiments herein, for distinguishing between subjects with abnormal or normal CT scan results. FIG. 10B shows the results of a non-dual capture assay for distinguishing between subjects with abnormal or normal CT scan results.

DETAILED DESCRIPTION OF THE INVENTION

Figure 2B:
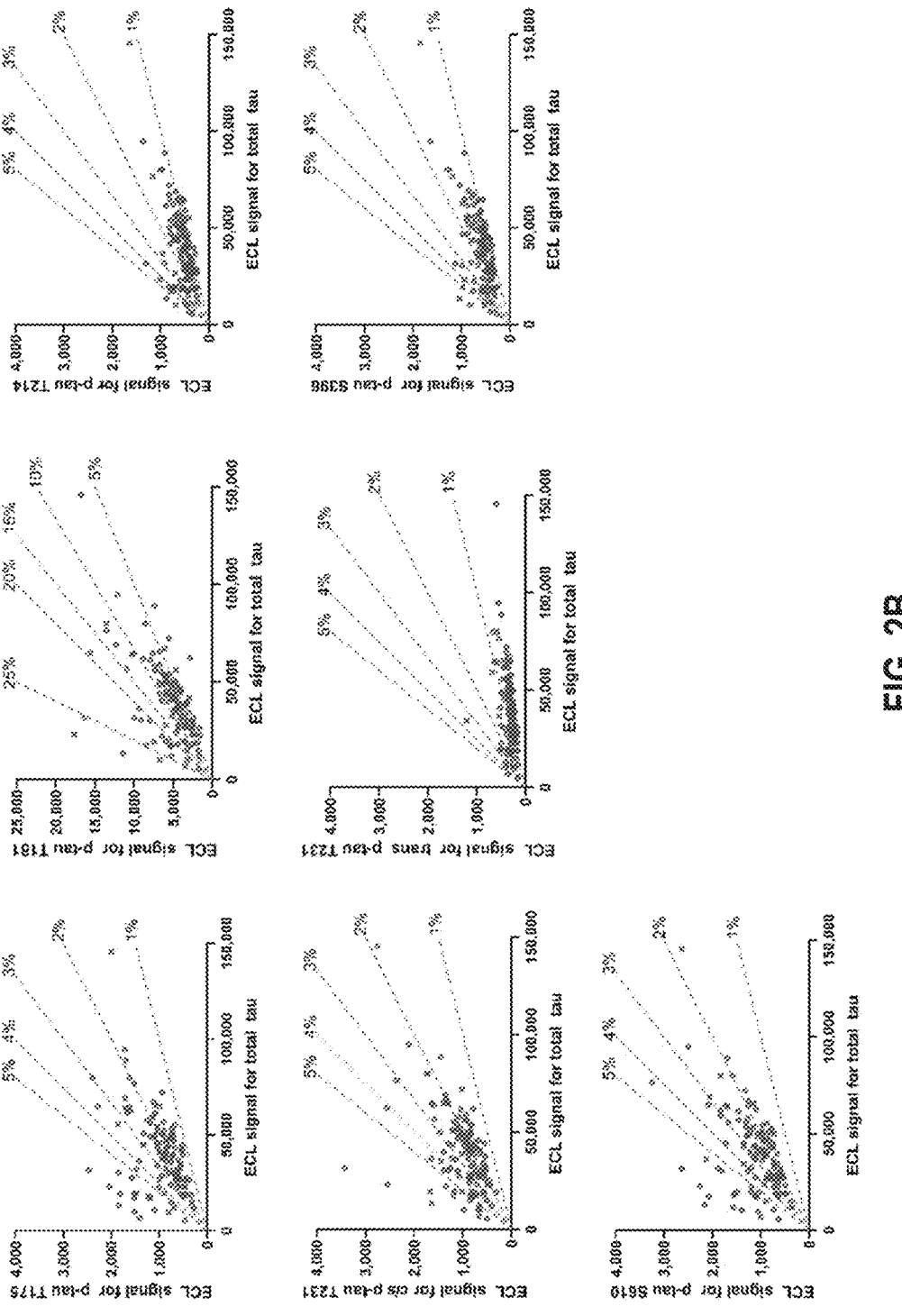
FIG. 2B shows the results from ECL-based immunoassays for p-tau at different phosphorylation sites, plotted against total tau. Each circle represents a serum sample. Dashed lines indicate the labeled percentage of total tau signal. The expected signals due to cross-reactivity with total tau are between 1% to 2%.

Unless otherwise defined herein, scientific and technical terms used in the present disclosure shall have the meanings that are commonly understood by one of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The use of the term "or" in the claims is used to mean "and/or," unless explicitly indicated to refer only to alternatives or the alternatives are mutually exclusive, although the disclosure supports a definition that refers to only alternatives and "and/or."

As used herein, the terms "comprising" (and any variant or form of comprising, such as "comprise" and "comprises"), "having" (and any variant or form of having, such as "have" and "has"), "including" (and any variant or form of including, such as "includes" and "include") or "containing" (and any variant or form of containing, such as "contains" and "contain") are inclusive or open-ended and do not exclude additional, unrecited, elements or method steps.

The use of the term "for example" and its corresponding abbreviation "e.g." (whether italicized or not) means that the specific terms recited are representative examples and embodiments of the invention that are not intended to be limited to the specific examples referenced or cited unless explicitly stated otherwise.

As used herein, "between" is a range inclusive of the ends of the range. For example, a number between x and y explicitly includes the numbers x and y, and any numbers that fall within x and y.

In embodiments, measurement of biomarker values and levels before and after a particular event, e.g., cellular or environmental event, are used to gain information regarding an individual's response to the event. For example, samples or model organisms are subjected to stress- or disease-inducing conditions, or a treatment or prevention regimen, and a particular biomarker is then detected and quantitated in order to determine its changes in response to the condition or regimen. The opposite, i.e., measuring biomarker values and levels to determine whether an organism has been subjected to stress- or disease-inducing condition, tends to be much more complicated, as changes in the levels of a single biomarker typically cannot be definitively associated with a particular condition. However, in some cases, a single biomarker can be strongly correlated with a condition. In such cases, a highly sensitive and specific detection method for the single biomarker is important for assessing the condition and/or providing an appropriate treatment.

The methods of the invention provide several advantages. For instance, the methods herein have improved sensitivity, specificity, and accuracy as compared to methods described in the art. In embodiments, the invention provides a simple, convenient, sensitive, and specific assay with a wide dynamic range for detecting and/or quantifying phosphorylated tau ("p-tau").

In embodiments, the method utilizes two capture reagents and one or more detection reagents that bind p-tau in a particular configuration as described herein. In embodiments, the first and second capture reagents bind p-tau with higher affinity and greater specificity as compared with a single capture reagent, thereby providing improved sensitivity and specificity. In embodiments, the capture reagents are capable of binding p-tau or non-phosphorylated tau. In embodiments, at least one detection reagent binds p-tau but not non-phosphorylated tau. In embodiments, the method has decreased cross-reactivity with non-phosphorylated tau and improved accuracy for p-tau.

In embodiments, the invention further provides a simple, convenient, sensitive, and specific assay with a wide dynamic range for detecting and/or quantifying total tau ("t-tau"). In embodiments, the method utilizes two capture reagents and one or more detection reagents that bind tau. In embodiments, the first and second capture reagents bind tau with higher affinity and greater specificity as compared with a single capture reagent, thereby improving sensitivity and specificity. In embodiments, the capture reagents are capable of binding p-tau or non-phosphorylated tau.

Tau

In embodiments, the present invention provides methods for quantifying the amount of phosphorylated tau (p-tau) in a biological sample. In embodiments, the present invention provides methods for quantifying the amount of total tau (t-tau) in a biological sample.

The tau protein can be found in neurons of the central nervous system (CNS) and, to a lesser extent, in CNS astrocytes and oligodendrocytes. Tau is primarily involved in maintaining the stability of microtubules in axons by interacting with tubulin and promoting tubulin assembly into microtubules. Tau has also been shown to play a role in cellular signaling protein recruitment, microtubule-mediated axonal transport regulation, neuronal development, neuroprotection, and apoptosis. Wang et al., Prog Neurobiol 85(2):148-175 (2008); Cleveland et al., J Mol Biol 116(2):207-225 (1977); Papanikolopoulou et al., J Neurosci 39(42):8315-8329 (2019).

Tau is a phosphoprotein with 79 potential serine (Ser) and threonine (Thr) phosphorylation sites on the longest tau isoform; phosphorylation has been observed at about 30 of these sites. The phosphorylated form of tau is commonly referred to as "p-tau." Phosphorylation of tau is regulated by a host of kinases, including protein kinase N1 (PKN). When PKN is activated, it phosphorylates tau, resulting in disruption of microtubule organization. Taniguchi et al., J Biol Chem 276(13):10025-10031 (2001). Cellular phosphatases also play a role in regulating the phosphorylation of tau. For example, protein phosphatases 2A (PP2A) and 2B (PP2B) are both present in human brain tissue and have the ability to dephosphorylate Ser396 of tau. The binding of these phosphatases to tau can affect tau's association with microtubules. Matsuo et al., Neuron 13(4):989-1002 (1994). Accumulation of hyperphosphorylated tau in neurons leads to neurofibrillary degeneration, which can cause various toxic effects. Hyperphosphorylation of tau can result in the self-assembly of tangles of paired helical filaments and straight filaments, which are involved in the pathogenesis of Alzheimer's disease, frontotemporal dementia, and other tauopathies. Alonso et al., Proc Natl Acad Sci USA 98(12): 6923-6928 (2001). McKee et al., Brain 136 (Pt 1):43-64 (2013); Omalu et al., Neurosurgery 57(1):128-134 (2005); Stern et al., N Engl J Med 380(18):1716-1725 (2019).

Tau accumulation can also lead to chronic traumatic encephalopathy (CTE), and high levels of tau and p-tau have been observed in the brains of retired professional American football players and blast-exposed military veterans. Goldstein et al., Sci Transl Med 4(134):134ra60 (2012); Rubenstein et al., JAMA Neurol 74(9):1063-1072 (2017). Thus, tau and p-tau may be important biomarkers for assessment and diagnosis of traumatic brain injury (TBI), e.g., blast-related brain injury.

For high-risk individuals such as active combat military personnel, early detection and diagnosis of traumatic brain injury, e.g., by measuring the individual's p-tau levels, can be critical for treatment and recovery. Measurement of p-tau can be a challenging task, as typical assay methods do not sufficiently distinguish between non-phosphorylated and phosphorylated tau. Moreover, p-tau is generally a relatively small proportion of the total tau present in a biological sample. In embodiments, the methods herein provide a simple, convenient, sensitive, and specific method with a wide dynamic range for quantifying the amount of phosphorylated tau (p-tau) in a biological sample.

In embodiments, the invention provides a method of quantifying the amount of phosphorylated tau (p-tau) in a biological sample, comprising: (a) contacting the biological sample with: (i) a first capture reagent that binds non-phosphorylated tau; (ii) a second capture reagent that binds non-phosphorylated tau, wherein the first and second capture reagents are on a surface, and the surface further comprises an anchoring reagent; (iii) a first detection reagent that binds non-phosphorylated tau, wherein the first detection reagent comprises a first nucleic acid probe; and (iv) a second detection reagent that binds p-tau, wherein the second detection reagent comprises a second nucleic acid probe, thereby forming a complex on the surface comprising the first and second capture reagents, p-tau, and the first and second detection reagents; (b) using an extension process that requires the first and second nucleic acid probes to be in proximity, extending the second nucleic acid probe to form an extended sequence comprising an anchoring region that binds to the anchoring reagent; (c) binding the extended sequence to the anchoring reagent; and (d) measuring the amount of extended sequence bound to the surface, thereby quantifying the amount of p-tau.

In embodiments, the invention provides a method of quantifying the amount of phosphorylated tau (p-tau) in a biological sample, comprising: (a) contacting the biological sample with: (i) a first capture reagent that binds non-phosphorylated tau; (ii) a second capture reagent that binds non-phosphorylated tau, wherein the first and second capture reagents are on a surface, and the surface further comprises an anchoring reagent; (iii) a detection reagent that binds p-tau, wherein the detection reagent comprises a nucleic acid probe, thereby forming a complex on the surface comprising the first and second capture reagents, p-tau, and the detection reagent; (b) extending the nucleic acid probe to form an extended sequence comprising an anchoring region that binds to the anchoring reagent; (c) binding the extended sequence to the anchoring reagent; and (d) measuring the amount of extended sequence bound to the surface, thereby quantifying the amount of p-tau.

In embodiments, the invention provides a method of quantifying the amount of phosphorylated tau (p-tau) in a biological sample, comprising: (a) contacting the biological sample with: (i) a first capture reagent that binds non-phosphorylated tau; (ii) a second capture reagent that binds non-phosphorylated tau, wherein the first and second capture reagents are on a surface; (iii) a detection reagent that binds p-tau, wherein the detection reagent comprises a detectable label, thereby forming a complex on the surface comprising the first and second capture reagents, p-tau, and the detection reagent; and (c) measuring the amount of detectable label on the surface, thereby quantifying the amount of p-tau.

In embodiments, the p-tau is phosphorylated at amino acid position T175, T181, T212, S214, cis T231, trans T231, S293, S396, S610, or a combination thereof, wherein the amino acid position corresponds to SEQ ID NO:1. Unless otherwise specified, all amino acid residues of tau or p-tau referenced herein correspond to SEQ ID NO:1. In embodiments, the p-tau is phosphorylated at T175 ("pT175-tau"). In embodiments, the p-tau is phosphorylated at T181 ("pT181-tau"). In embodiments, the p-tau is phosphorylated at T212 ("pT212-tau"). In embodiments, the p-tau is phosphorylated at S214 ("pS214-tau"). In embodiments, the p-tau is phosphorylated at cis T231 ("pcisT231-tau"). In embodiments, the p-tau is phosphorylated at trans T231 ("ptransT231-tau"). In embodiments, the p-tau is phosphorylated at S293 ("pS293-tau"). In embodiments, the p-tau is phosphorylated at S396 ("pS396-tau"). In embodiments, the p-tau is phosphorylated at S610 ("pS610-tau"). As discussed herein, tau has a number of serine and threonine residues that can be phosphorylated. Phosphorylation of tau at T175, T181, T212, S214, cis T231, trans T231, S293, S396, S610, or a combination thereof was unexpectedly discovered to have a high correlation with blast-related TBI, and particularly in subjects with repeated blast exposures.

In embodiments, the invention provides a method of quantifying the amount of total tau (t-tau) in a biological sample, comprising: (a) contacting the biological sample with: (i) a first capture reagent that binds tau; (ii) a second capture reagent that binds tau, wherein the first and second capture reagents are on a surface, and the surface further comprises an anchoring reagent; (iii) a first detection reagent that binds tau, wherein the first detection reagent comprises a first nucleic acid probe; and (iv) a second detection reagent that binds tau, wherein the second detection reagent comprises a second nucleic acid probe, thereby forming a complex on the surface comprising the first and second capture reagents, tau, and the first and second detection reagents; (b) using an extension process that requires the first and second nucleic acid probes to be in proximity, extending the second nucleic acid probe to form an extended sequence comprising an anchoring region that binds to the anchoring reagent; (b) binding the extended sequence to the anchoring reagent; and (c) measuring the amount of extended sequence bound to the surface, thereby quantifying the amount of t-tau. In embodiments, the first and second capture reagents and the first and second detection reagents are capable of binding to phosphorylated and non-phosphorylated tau.

In embodiments, the invention provides a method of quantifying the amount of total tau (t-tau) in a biological sample, comprising: (a) contacting the biological sample with: (i) a first capture reagent that binds tau; (ii) a second capture reagent that binds tau, wherein the first and second capture reagents are on a surface, and the surface further comprises an anchoring reagent; (iii) a detection reagent that binds tau, wherein the detection reagent comprises a nucleic acid probe, thereby forming a complex on the surface comprising the first and second capture reagents, tau, and the detection reagent; (b) extending the nucleic acid probe to form an extended sequence comprising an anchoring region that binds to the anchoring reagent; (c) binding the extended sequence to the anchoring reagent; and (d) measuring the amount of extended sequence bound to the surface, thereby quantifying the amount of t-tau. In embodiments, the first and second capture reagents and the detection reagent are capable of binding to phosphorylated and non-phosphorylated tau.

In embodiments, the invention provides a method of quantifying the amount of total tau (t-tau) in a biological sample, comprising: (a) contacting the biological sample with: (i) a first capture reagent that binds tau; (ii) a second capture reagent that binds tau, wherein the first and second capture reagents are on a surface; (iii) a detection reagent that binds tau, wherein the detection reagent comprises a detectable label, thereby forming a complex on the surface comprising the first and second capture reagents, tau, and the detection reagent; and measuring the amount of detectable label on the surface, thereby quantifying the amount of tau. In embodiments, the first and second capture reagents and the detection reagent are capable of binding to phosphorylated and non-phosphorylated tau.

Capture Reagent

In embodiments, the invention provides methods utilizing two capture reagents (i.e., first and second capture reagents) that bind to an analyte of interest, e.g., p-tau or non-phosphorylated tau, referred to herein as a "dual-capture" assay. In embodiments, the two capture reagents of a dual-capture assay bind synergistically to the analyte of interest, e.g., p-tau or non-phosphorylated tau. As used herein, "synergistic binding" refers to a higher binding affinity when using two binding reagents compared with the sum of each binding reagent's individual binding affinity. In embodiments, the capture reagents of a dual-capture assay bind the analyte of interest, e.g., p-tau or non-phosphorylated tau, with higher affinity compared with a single capture reagent. In embodiments, the capture reagents of a dual-capture assay bind the analyte of interest, e.g., p-tau or non-phosphorylated tau, with greater specificity compared with a single capture reagent. In embodiments, a dual-capture assay has improved sensitivity and/or specificity relative to an assay utilizing a single capture reagent.

In embodiments, the first capture reagent is an antibody, antigen, ligand, receptor, oligonucleotide, hapten, epitope, mimotope, or an aptamer. In embodiments, the first capture reagent is an antibody or a variant thereof, including an antigen/epitope-binding portion thereof, an antibody fragment or derivative, an antibody analogue, an engineered antibody, or a substance that binds to antigens in a similar manner to antibodies. In embodiments, the first capture reagent comprises at least one heavy or light chain complementarity determining region (CDR) of an antibody. In embodiments, the first capture reagent comprises at least two CDRs from one or more antibodies. In embodiments, the first capture reagent is an antibody or antigen-binding fragment thereof.

In embodiments, the first capture reagent is capable of binding to non-phosphorylated tau. In embodiments, the first capture reagent is capable of binding to p-tau. In embodiments, the first capture reagent is capable of binding to non-phosphorylated tau and p-tau. In embodiments, the first capture reagent is capable of binding to p-tau that is phosphorylated at T175, T181, T212, 5214, cis T231, trans T231, 5293, 5396, 5610, or a combination thereof.

In embodiments, the second capture reagent is an antibody, antigen, ligand, receptor, oligonucleotide, hapten, epitope, mimotope, or an aptamer. In embodiments, the second capture reagent is an antibody or a variant thereof, including an antigen/epitope-binding portion thereof, an antibody fragment or derivative, an antibody analogue, an engineered antibody, or a substance that binds to antigens in a similar manner to antibodies. In embodiments, the second capture reagent comprises at least one heavy or light chain complementarity determining region (CDR) of an antibody. In embodiments, the second capture reagent comprises at least two CDRs from one or more antibodies. In embodiments, the second capture reagent is an antibody or antigen-binding fragment thereof.

In embodiments, the second capture reagent is capable of binding to non-phosphorylated tau. In embodiments, the second capture reagent is capable of binding to p-tau. In embodiments, the second capture reagent is capable of binding to non-phosphorylated tau and p-tau. In embodiments, the second capture reagent is capable of binding to p-tau that is phosphorylated at T175, T181, T212, 5214, cis T231, trans T231, S293, S396, 5610, or a combination thereof.

In embodiments, each of the first and second capture reagents is an antibody or antigen-binding fragment thereof. In embodiments, each of the first and second capture reagents binds to non-phosphorylated tau. In embodiments, each of the first and second capture reagents that bind non-phosphorylated tau is capable of binding p-tau. In embodiments, each of the first and second capture reagents is capable of binding to p-tau is phosphorylated at T175, T181, T212, 5214, cis T231, trans T231, S293, S396, 5610, or a combination thereof. In embodiments, the first and second capture reagents are the antibodies MSD clone AA-26-VEC0983-0981 and MSD clone AA-25-VEC0728-0727 (Meso Scale Diagnostics, Rockville, MD, USA, "MSD").

Detection Reagent

In embodiments comprising first and second detection reagents, the first detection reagent is an antibody, antigen, ligand, receptor, oligonucleotide, hapten, epitope, mimotope, or an aptamer. In embodiments, the first detection reagent is an antibody or a variant thereof, including an antigen/epitope-binding portion thereof, an antibody fragment or derivative, an antibody analogue, an engineered antibody, or a substance that binds to antigens in a similar manner to antibodies. In embodiments, the first detection reagent comprises at least one heavy or light chain complementarity determining region (CDR) of an antibody. In embodiments, the first detection reagent comprises at least two CDRs from one or more antibodies. In embodiments, the first detection reagent is an antibody or antigen-binding fragment thereof.

In embodiments comprising first and second detection reagents, the first detection reagent is capable of binding to non-phosphorylated tau. In embodiments, the first detection reagent is capable of binding to p-tau. In embodiments, the first detection reagent is capable of binding to p-tau that is phosphorylated at T175, T181, T212, 5214, cis T231, trans T231, 5293, S396, 5610, or a combination thereof.

In embodiments comprising first and second detection reagents, the second detection reagent is an antibody, antigen, ligand, receptor, oligonucleotide, hapten, epitope, mimotope, or an aptamer. In embodiments, the second detection reagent is an antibody or a variant thereof, including an antigen/epitope-binding portion thereof, an antibody fragment or derivative, an antibody analogue, an engineered antibody, or a substance that binds to antigens in a similar manner to antibodies. In embodiments, the second detection reagent comprises at least one heavy or light chain complementarity determining region (CDR) of an antibody. In embodiments, the second detection reagent comprises at least two CDRs from one or more antibodies. In embodiments, the second detection reagent is an antibody or antigen-binding fragment thereof.

In embodiments where the method detects p-tau and comprises first and second detection reagents, the second detection reagent is capable of binding to p-tau. In embodiments, the second detection reagent is capable of binding to p-tau that is phosphorylated at T175, T181, T212, 5214, cis T231, trans T231, S293, S396, 5610, or a combination thereof. In embodiments, the second detection reagent does not bind non-phosphorylated tau. In embodiments, the method utilizing a second detection reagent that binds p-tau, but not non-phosphorylated tau, has improved specificity compared with a method that utilizes a second detection reagent that is capable of binding non-phosphorylated tau.

In embodiments where the method detects t-tau and comprises first and second detection reagents, the second detection reagent is capable of binding to non-phosphorylated tau. In embodiments, the second detection reagent is capable of binding to p-tau. In embodiments, the second detection reagent is capable of binding to p-tau that is phosphorylated at T175, T181, T212, 5214, cis T231, trans T231, S293, S396, 5610, or a combination thereof.

In embodiments comprising a detection reagent, the detection reagent is an antibody, antigen, ligand, receptor, oligonucleotide, hapten, epitope, mimotope, or an aptamer. In embodiments, the detection reagent is an antibody or a variant thereof, including an antigen/epitope-binding portion thereof, an antibody fragment or derivative, an antibody analogue, an engineered antibody, or a substance that binds to antigens in a similar manner to antibodies. In embodiments, the detection reagent comprises at least one heavy or light chain complementarity determining region (CDR) of an antibody. In embodiments, the detection reagent comprises at least two CDRs from one or more antibodies. In embodiments, the detection reagent is an antibody or antigen-binding fragment thereof.

In embodiments where the method detects p-tau and comprises a detection reagent, the detection reagent binds to p-tau. In embodiments, the detection reagent is capable of binding to p-tau that is phosphorylated at T175, T181, T212, 5214, cis T231, trans T231, 5293, 5396, S610, or a combination thereof. In embodiments, the detection reagent does not bind non-phosphorylated tau. In embodiments, the method utilizing a detection reagent that binds p-tau, but not non-phosphorylated tau, has improved specificity compared with a method that utilizes a detection reagent that is capable of binding non-phosphorylated tau. In embodiments, the detection reagent is the antibody MSD clone AA-114-VEC1367-1366. In embodiments, the detection reagent that binds to p-tau that is phosphorylated at T175 is the antibody MSD clone 4608-C46-1 In embodiments, the detection reagent that binds to p-tau that is phosphorylated at cis T231 is the antibody MSD clone 4644-J87-1.

In embodiments where the method detects t-tau and comprises a detection reagent, the detection reagent is capable of binding to non-phosphorylated tau. In embodiments, the detection reagent is capable of binding to p-tau. In embodiments, the detection reagent is capable of binding to p-tau that is phosphorylated at T175, T181, T212, 5214, cis T231, trans T231, S293, S396, 5610, or a combination thereof. In embodiments, the detection reagent is the antibody MSD clone AA-114-VEC1367-1366. In embodiments, the detection reagent that binds to p-tau that is phosphorylated at T175 is the antibody MSD clone 4608-C46-1. In embodiments, the detection reagent that binds to p-tau that is phosphorylated at cis T231 is the antibody MSD clone 4644-J87-1.

Extending Step

In embodiments where the first and second detection reagents respectively comprise first and second nucleic acid probes, the extending step of the method comprises binding the first and second nucleic acid probes of the first and second detection reagents to a template oligonucleotide. In embodiments, the first and second nucleic acid probes bind to the template oligonucleotide when the first and second nucleic acid probes are in proximity, e.g., when the first and second detection reagents are bound to the analyte, e.g., tau or p-tau. In embodiments, the extending step comprises binding the first and second nucleic acid probes to a template oligonucleotide and extending the second nucleic acid probe by polymerase chain reaction (PCR), ligase chain reaction (LCR), strand displacement amplification (SDA), self-sustained synthetic reaction (3SR), isothermal amplification (such as, e.g., helicase-dependent amplification or rolling circle amplification), or combination thereof. In embodiments, the extending step comprises binding the first and second nucleic acid probes to a template oligonucleotide and extending the second nucleic acid probe by PCR. In embodiments, the extending step comprises the extending step comprises binding the first and second nucleic acid probes to a template oligonucleotide, forming a circular template oligonucleotide (e.g., by ligation of a linear template oligonucleotide to form a circle), and extending the second nucleic acid probe by rolling circle amplification (RCA).

In embodiments where the first and second detection reagents respectively comprise first and second nucleic acid probes, the extending step of the method comprises contacting the complex comprising the first and second capture reagents, the analyte, e.g., tau or p-tau, and the first and second detection reagents with a connector sequence comprising (i) an interior sequence complementary to the second nucleic acid probe and (ii) two end sequences complementary to non-overlapping regions of the first nucleic acid probe. In embodiments, the method further comprises ligating the two end sequences of the connector oligonucleotide to form a circular template oligonucleotide that is hybridized to both the first and second nucleic acid probes, and extending the second nucleic acid probe by RCA. In embodiments, the extending step comprises contacting the complex with (i) a first connector oligonucleotide comprising a first connector probe sequence complementary to a first region of the first nucleic acid probe and a first region on the second nucleic acid probe, and (ii) a second connector oligonucleotide comprising a second connector probe sequence complementary to a second non-overlapping region of the first nucleic acid probe and a second non-overlapping region of the second nucleic acid probe. In embodiments, the method further comprises ligating the first and second connector oligonucleotides to form a circular template oligonucleotide that is hybridized to both the first and second nucleic acid probes, and extending the second nucleic acid probe by RCA.

In embodiments where the detection reagent comprises a nucleic acid probe, the extending step of the method comprises binding the nucleic acid probe of the detection reagent to a template oligonucleotide. In embodiments, the extending step comprises binding the nucleic acid probe to a template oligonucleotide and extending the nucleic acid probe by polymerase chain reaction (PCR), ligase chain reaction (LCR), strand displacement amplification (SDA), self-sustained synthetic reaction (3SR), isothermal amplification (such as, e.g., helicase-dependent amplification or rolling circle amplification), or combination thereof. In embodiments, the extending step comprises binding the nucleic acid probe of the detection reagent to a template oligonucleotide and extending the nucleic acid probe by polymerase chain reaction (PCR). In embodiments, the extending step comprises binding the nucleic acid probe to a template oligonucleotide, forming a circular template oligonucleotide (e.g., by ligation of a linear template oligonucleotide to form a circle), and extending the nucleic acid probe by rolling circle amplification.

Anchoring Reagent

In embodiments comprising an anchoring reagent, the anchoring reagent comprises an oligonucleotide, aptamer, aptamer ligand, antibody, antigen, ligand, receptor, hapten, epitope, or a mimotope. In embodiments, the anchoring reagent comprises an aptamer ligand, and the anchoring region of the extended sequence comprises an aptamer. In embodiments, the anchoring reagent comprises an oligonucleotide-binding protein, and the anchoring region of the extended sequence comprises an oligonucleotide sequence. In embodiments, the anchoring reagent comprises a single stranded oligonucleotide. In embodiments, the anchoring reagent comprises a double stranded oligonucleotide. In embodiments, the anchoring reagent and the anchoring region comprise complementary oligonucleotide sequences. In embodiments, the anchoring reagent comprises an anchoring oligonucleotide. In embodiments, the extended sequence comprises an anchoring oligonucleotide complement that is complementary to the anchoring oligonucleotide.

In embodiments comprising an extended sequence, binding the extended sequence to the anchoring reagent comprises forming a triple helix between the anchoring reagent and the anchoring region. In embodiments, binding the extended sequence to the anchoring reagent comprises denaturing the anchoring region to expose a single stranded oligonucleotide region prior to the binding step; exposing the anchoring region to helicase activity prior to the binding step; and/or exposing the anchoring region to nuclease treatment prior to the binding step, wherein the anchoring region comprises one or more hapten-modified bases and the anchoring reagent comprises one or more antibodies specific for the hapten; and/or the anchoring region comprises one or more ligand-modified bases and the anchoring reagent comprises one or more receptors specific for the ligand.

Measuring Step

In embodiments, measuring the amount of extended sequence comprises contacting the extended sequence with a labeled probe that binds to the extended sequence. In embodiments, the extended sequence comprises a detection sequence complement that is complementary to a detection oligonucleotide, and measuring the amount of extended sequence comprises contacting the extended sequence with a labeled probe comprising the detection oligonucleotide and a detectable label. In embodiments, the extended sequence comprises a modified base, and measuring the amount of extended sequence comprises contacting the extended sequence with a detectable moiety capable of binding to the modified base. In embodiments, the modified base comprises an aptamer, aptamer ligand, antibody, antigen, ligand, receptor, hapten, epitope, or a mimotope, and the detectable moiety comprises a binding partner of the modified base and a detectable label. In embodiments, the modified base comprises streptavidin, and the detectable moiety comprises biotin and a detectable label. In embodiments, the modified base comprises avidin, and the detectable moiety comprises biotin and a detectable label. In embodiments, the modified base comprise biotin, and the detectable moiety comprises avidin and a detectable label.

In embodiments comprising a labeled probe or a detectable moiety that comprises a detectable label, the detectable label is measured by a measurement of light scattering, optical absorbance, fluorescence, chemiluminescence, electrochemiluminescence, bioluminescence, phosphorescence, radioactivity, magnetic field, or combinations thereof. In embodiments, the detectable label is an electrochemiluminescent (ECL) label, and measuring the extended sequence comprises measuring an ECL signal. In embodiments, the labeled probe or detectable moiety comprises multiple detectable labels, e.g., multiple ECL labels. In embodiments, the detectable label comprises ruthenium. In embodiments, the amount of measured ECL signal is used to determine the amount of p-tau in the biological sample. In embodiments, the amount of measured ECL signal is used to determine the amount of t-tau in the biological sample.

In embodiments where the detection reagent comprises a detectable label, the measuring step of the method comprises measuring the presence and/or amount of the detectable label. In embodiments, the detectable label is measured by light scattering, optical absorbance, fluorescence, chemiluminescence, electrochemiluminescence (ECL), bioluminescence, phosphorescence, radioactivity, magnetic field, or combinations thereof. In embodiments, the detectable label comprises an ECL label, and measuring the amount of detectable label comprises measuring an ECL signal. In embodiments, the detectable label comprises multiple ECL labels. In embodiments, the detectable label comprises ruthenium. In embodiments, the amount of measured ECL signal is used to determine the amount of p-tau in the biological sample. In embodiments, the amount of measured ECL signal is used to determine the amount of t-tau in the biological sample.

Immobilized and Solution Formats

In embodiments, the first and second capture reagents are immobilized to the surface. In embodiments, the first and second capture reagents are directly immobilized on the surface. In embodiments, the first and second capture reagents are indirectly immobilized on the surface via secondary binding reagents, e.g., a targeting agent. In embodiments, each of the first and second capture reagents is linked to a targeting agent complement that binds to a targeting agent immobilized on the surface. In embodiments, the targeting agent complement directly binds to the targeting agent. In embodiments, the targeting agent and targeting agent complement comprise complementary oligonucleotides, a receptor-ligand pair, an antigen-antibody pair, a hapten-antibody pair, an epitope-antibody pair, a mimotope-antibody pair, an aptamer-target molecule pair, hybridization partners, or an intercalator-target molecule pair. In embodiments, the targeting agent and targeting agent complement are cross-reactive moieties, e.g., thiol and maleimide or iodoacetamide; aldehyde and hydrazide; or azide and alkyne or cycloalkyne. In embodiments, the targeting agent is biotin, and the targeting agent complement is avidin or streptavidin. In embodiments, the targeting agent and targeting agent complement are selected such that the targeting agent and targeting agent complement associated with the first capture reagent are substantially non-cross-reactive with the targeting agent and targeting agent complement associated with the second capture reagent. In embodiments, the same targeting agent and targeting complement pair is associated with the first and second capture reagents.

In embodiments comprising first and second detection reagents, the method comprises binding the analyte, e.g., tau or p-tau, to the first and second detection reagents in solution to form a first complex, contacting the first complex to the first and second capture reagents on the surface to form a second complex comprising the first and second capture reagents, the analyte, e.g., tau or p-tau, and the first and second detection reagents, then extending the second nucleic acid probe as described herein. In embodiments, the method comprises binding the analyte, e.g., tau or p-tau to the first and second detection reagents in solution to form a first complex, extending the second nucleic acid probe as described herein to form an extended sequence, then binding the extended sequence to the surface via the first and second capture reagents and/or the anchoring reagent.

In embodiments comprising a detection reagent that comprises a nucleic acid probe, the method comprises binding the analyte, e.g., tau or p-tau to the detection reagent in solution to form a first complex, contacting the first complex to the first and second capture reagents on the surface to form a second complex comprising the first and second capture reagents, the analyte, e.g., tau or p-tau, and the detection reagent, then extending the nucleic acid probe as described herein. In embodiments, the method comprises binding the analyte, e.g., tau or p-tau to the detection reagent in solution to form a first complex, extending the nucleic acid probe as described herein to form an extended sequence, then binding the extended sequence to the surface via the first and second capture reagents and/or the anchoring reagent.

In embodiments comprising a detection reagent that comprises a detectable label, the method comprises binding the analyte, e.g., tau or p-tau to the detection reagent in solution to form a first complex, contacting the first complex to the first and second capture reagents on the surface to form a second complex comprising the first and second capture reagents, the analyte, e.g., tau or p-tau, and the detection reagent, then measuring the amount of detectable label as described herein.

In embodiments comprising an anchoring reagent, the anchoring reagent is immobilized to the surface. In embodiments, the anchoring reagent is directly immobilized on the surface. In embodiments, the anchoring reagent is indirectly immobilized on the surface via secondary binding reagents, e.g., a targeting reagent as described herein. In embodiments, the targeting agent and targeting agent complement for the anchoring reagent is selected such that the targeting agent and targeting agent complement associated with the anchoring reagent are substantially non-cross-reactive with the targeting agent and targeting agent complement associated with the first and second capture reagents. In embodiments, the same targeting agent and targeting complement pair is associated with the first and second capture reagents and the anchoring reagent.

In embodiments, the targeting agent complement binds to the targeting agent via a targeting bridge agent, which is a binding partner of both the targeting agent and the targeting agent complement. In embodiments, the targeting bridge agent comprises multiple binding sites. In embodiments, the targeting bridge agent is streptavidin or avidin, and the targeting agent and targeting agent complement are each biotin.

Surface

In embodiments, the surface comprises a particle. In embodiments, the surface comprises a well of multi-well plate. In embodiments, the surface comprises a plurality of distinct binding domains, and the first capture reagent, the second capture reagent, and the anchoring reagent are located on two or more distinct binding domains on the surface. In embodiments where the surface comprises a well, the surface comprises a plurality of distinct binding domains, and the first capture reagent, the second capture reagent, and the anchoring reagent are located on two or more distinct binding domains within the well. In embodiments, the surface comprises a plurality of distinct binding domains, and first capture reagent, the second capture reagent, and the anchoring reagent are located on the same binding domain on the surface. In embodiments where the surface comprises a well, the surface comprises a plurality of distinct binding domains, and the first capture reagent, the second capture reagent, and the anchoring reagent are located on the same binding domain within the well.

In embodiments, the surface comprises an electrode. In embodiments, the electrode is a carbon ink electrode. In embodiments, measuring the amount of extended sequence comprises applying a voltage waveform (e.g., a potential) to the electrode to general an ECL signal. In embodiments, the surface comprises a particle, and the method comprises collecting the particle on an electrode and applying a voltage waveform (e.g., a potential) to the electrode to generate an ECL signal.

Multiplex

As discussed herein, p-tau can be phosphorylated at various amino acid residues (also termed "sites"), and levels of p-tau phosphorylated at certain sites have been shown to increase with traumatic brain injury. In embodiments, levels of p-tau phosphorylated at T175, T181, T212, 5214, cis T231, trans T231, 5293, 5396, 5610, or a combination thereof are elevated in subjects with TBI. In embodiments, levels of p-tau phosphorylated at T175, T181, T212, 5214, cis T231, trans T231, S293, S396, 5610, or a combination thereof are higher in subjects with repeated blast exposures. Thus, quantifying a combination of p-tau that is phosphorylated at various sites, e.g., a combination of T175, T181, T212, 5214, cis T231, trans T231, S293, S396, and/or 5610, can provide a more consistent and accurate assessment and/or diagnosis of traumatic brain injury. In embodiments, the method quantifies the amount of p-tau that is phosphorylated at each of T175, T181, T212, 5214, cis T231, trans T231, S293, S396, and S610. In embodiments, levels of total tau are elevated with subjects with TBI. In embodiments, the method further quantifies the amount of non-phosphorylated tau. In embodiments, the method quantifies the amount of non-phosphorylated tau and the amount of p-tau that is phosphorylated at each of T175, T181, 5214, cis T231, trans T231, S293, and S396.

In embodiments where the method detects p-tau, different detection reagents are used for p-tau phosphorylated at each site. In embodiments comprising first and second detection reagents, the biological sample is contacted with: (i) the first and second capture reagents and the first detection reagent that binds non-phosphorylated tau as described herein, and (ii) a plurality of second detection reagents, each of which specifically binds a p-tau that is phosphorylated at a different site. In embodiments, the biological sample is simultaneously contacted with the plurality of second detection reagents. In embodiments, the biological sample is sequentially contacted with each second detection reagent of the plurality of second detection reagents. In embodiments, the biological sample is simultaneously or sequentially contacted with one or more of: a second detection reagent that binds non-phosphorylated tau, a second detection reagent that binds pT175-tau, a second detection reagent that binds pT181-tau, a second detection reagent that binds pT212-tau, a second detection reagent that binds pS214-tau, a second detection reagent that binds pcisT231-tau, a second detection reagent that binds ptransT231-tau, a second detection reagent that binds pS293-tau, a second detection reagent that binds pS396-tau, and a second detection reagent that binds pS610-tau. In embodiments, one or more subsequent method steps (e.g., the extending, binding, and/or measuring as described herein) are performed in parallel.

In embodiments comprising a detection reagent, the biological sample is contacted with: (i) the first and second capture reagents that binds non-phosphorylated tau as described herein, and (ii) a plurality of detection reagents, each of which specifically binds a p-tau that is phosphorylated at a different site. In embodiments, the biological sample is simultaneously contacted with the plurality of detection reagents. In embodiments, the biological sample is sequentially contacted with each detection reagent of the plurality of detection reagents. In embodiments, the biological sample is simultaneously or sequentially contacted with one or more of: a detection reagent that binds non-phosphorylated tau, a detection reagent that binds pT175-tau, a detection reagent that binds pT181-tau, a detection reagent that binds pT212-tau, a detection reagent that binds pS214-tau, a detection reagent that binds pcisT231-tau, a detection reagent that binds ptransT231-tau, a detection reagent that binds pS293-tau, a detection reagent that binds pS396-tau, and a detection reagent that binds pS610-tau. In embodiments, one or more subsequent method steps (e.g., the extending, binding, and/or measuring as described herein) are performed in parallel.

Sample

In embodiments, tau, e.g., non-phosphorylated tau or p-tau, is present in a biological sample. In embodiments, the biological sample comprises a mammalian fluid, secretion, or excretion. In embodiments, the biological sample is a purified mammalian fluid, secretion, or excretion. In embodiments, the mammalian fluid, secretion, or excretion is whole blood, plasma, serum, sputum, lachrymal fluid, lymphatic fluid, synovial fluid, pleural effusion, urine, sweat, cerebrospinal fluid, ascites, milk, stool, bronchial lavage, saliva, amniotic fluid, nasal secretions, vaginal secretions, a surface biopsy, sperm, semen/seminal fluid, wound secretions and excretions, or an extraction or purification therefrom, or dilution thereof. Further exemplary biological samples include but are not limited to physiological samples, samples containing suspensions of cells such as mucosal swabs, tissue aspirates, tissue homogenates, cell cultures, and cell culture supernatants. In embodiments, the biological sample is whole blood, serum, plasma, cerebrospinal fluid, urine, saliva, or an extraction or purification therefrom, or dilution thereof. In embodiments, the biological sample is serum or plasma. In embodiments, the plasma is in EDTA, heparin, or citrate. In embodiments, the biological sample is a mammalian fluid, secretion, or excretion that is known to contain a high level of tau, e.g., p-tau. In embodiments, the biological sample containing a high level of tau, e.g., p-tau is a control for the methods described herein. In embodiments, the biological sample containing a high level of tau, e.g., p-tau is cerebrospinal fluid (CSF), brain lysate (diluted or undiluted), or a combination thereof.

In embodiments, the biological sample comprises an exosome. An "exosome" refers to a small membrane vesicle that is released by most cell types. Exosomes have been shown to contain a wide variety of signaling molecules including but not limited to surface-bound and cytosolic proteins, lipids, mRNA, and miRNA, and the concentration of these species in each exosome can be linked to the amount present in the cell from which the exosome is released. In embodiments, the amount of p-tau or t-tau in an exosome is linked to the amount of p-tau or t-tau present in the cell from which the exosome is released.

In embodiments, the biological sample is obtained from a subject, e.g., a human subject. In embodiments, the biological sample comprises a plasma (e.g., in EDTA, heparin, or citrate) sample from a subject. In embodiments, the biological sample comprise a serum sample from a subject. In embodiments, the sample is obtained from a healthy subject. In embodiments, the biological sample is obtained from a subject that has not been exposed to a blast event. In embodiments, the biological sample is obtained from a subject exposed to a blast event, at risk of exposure to a blast event, or suspected of having been exposed to a blast event. In embodiments, the biological sample is obtained from a subject exposed to a known number of blast events. In embodiments, the biological sample is obtained from a subject having or at risk of disease, e.g., as a result of blast exposure.

Samples may be obtained from a single source described herein, or may contain a mixture from two or more sources, e.g., pooled from one or more subjects who may have been exposed to a blast event in a similar manner.

In embodiments, the biological sample is obtained from the subject within about 10 minutes to about 50 years, about 20 minutes to about 30 years, about 30 minutes to about 10 years, about 40 minutes to about 5 years, about 50 minutes to about 1 year, about 1 hour to about 6 months, about 6 hours to about 1 month, about 12 hours to about 2 weeks, about 1 day to about 7 days, about 2 days to about 6 days, or about 3 days to about 4 days after blast exposure or suspected blast exposure. In embodiments, the biological sample is obtained from the subject about 1 minute, about 10 minutes, about 30 minutes, about 1 hour, about 3 hours, about 6 hours, about 12 hours, about 24 hours, about 2 days, about 3 days, about 4 days, about 5 days, about 6 days, about 1 week, about 2 weeks, about 1 month, about 3 months, about 6 months, about 1 year, about 2 years, about 3 years, about 5 years, about 10 years, about 20 years, about 30 years, or more than 30 years after blast exposure or suspected blast exposure.

Blast Exposure

In embodiments, changes in a subject's tau, e.g., p-tau or t-tau levels are observable within minutes, hours, days, months, years and/or decades after blast exposure(s). In embodiments, changes in a subject's tau, e.g., p-tau or t-tau levels are observable about 10 minutes to about 50 years, about 20 minutes to about 30 years, about 30 minutes to about 10 years, about 40 minutes to about 5 years, about 50 minutes to about 1 year, about 1 hour to about 6 months, about 6 hours to about 1 month, about 12 hours to about 2 weeks, about 1 day to about 7 days, about 2 days to about 6 days, or about 3 days to about 4 days after blast exposure. In embodiments, changes in a subject's tau, e.g., p-tau or t-tau levels are observable about 1 minute, about 10 minutes, about 30 minutes, about 1 hour, about 3 hours, about 6 hours, about 12 hours, about 24 hours, about 2 days, about 3 days, about 4 days, about 5 days, about 6 days, about 1 week, about 2 weeks, about 1 month, about 3 months, about 6 months, about 1 year, about 2 years, about 3 years, about 5 years, about 10 years, about 20 years, about 30 years, about 50 years, or more than 50 years after blast exposure. In embodiments, changes in a subject's tau, e.g., p-tau or t-tau levels are observable when the subject has been exposed to one blast event, two blast events, three blast events, or three or more blast events. In embodiments, the method is used to monitor long-term effects of blast exposure in a subject, e.g., years or decades after the blast exposure.

In embodiments, a blast event comprises an explosion, e.g., from a conventional or improvised explosive device. In embodiments, blast exposure comprises exposure to a blast overpressure resulting from the shockwave produced by an explosion. In embodiments, blast exposure comprises an impact injury, e.g., due to debris from an explosion. In embodiments, blast exposure results in a blast-related brain injury. In embodiments, repeated blast exposure by a subject increases the likelihood of the subject to develop a blast-related brain injury. In embodiments, the blast-related brain injury comprises concussive injury, subconcussive injury, acute concussive injury, impact head injury, acceleration or deceleration head trauma, closed-skull neurotrauma, traumatic brain injury, stroke, seizure, status epilepticus, chronic traumatic encephalopathy (CTE), a neurodegenerative disease, or a combination thereof.

As discussed herein, early detection and diagnosis of traumatic brain injury, e.g., as a result of blast exposure, can be highly important for proper treatment. In some cases, traumatic brain injury does not manifest until days, months, years, or decades after the initial blast event or events. The present invention can be used to monitor risk and/or progression of traumatic brain injury. Moreover, determining the number of blast events that a subject, e.g., an active or retired combat personnel, can also aid in assessing the likelihood of developing a neurological condition or disease, such as CTE or a neurodegenerative disease such as Alzheimer's.

In embodiments, the invention provides a method for accurately determining the number of blast exposures experienced by the subject. In embodiments, the invention provides a method of determining the number of blast exposures experienced by a subject, comprising: (a) conducting the method provided herein on a biological sample of the subject to quantify the amount of p-tau in the biological sample; and (b) determining the number of blast exposures experienced by the subject based on the amount of p-tau. In embodiments, the method further comprises quantifying the amount of total tau (t-tau) in the biological sample, and determining the number of blast exposures experienced by the subject based on a ratio of the amount of p-tau to the amount of t-tau in the biological sample. In embodiments, the invention provides a method of determining the number of blast exposures experienced by a subject, comprising: (a) quantifying the amount of t-tau in a biological sample of the subject; and (b) determining the number of blast exposures experienced by the subject based on the amount of t-tau. In embodiments, total tau comprises phosphorylated and non-phosphorylated tau. In embodiments, the amount of t-tau in the biological sample is quantified by an immunoassay, mass spectrometry, or both. Measurement of tau is described in, e.g., US 2015/0119273 and Kenney et al., *Brain Injury* 32(10):1-9 (2018).

In embodiments, a method of quantifying the amount of t-tau in a biological sample comprises: (a) contacting the biological sample with: (i) a first capture reagent that binds tau; (ii) a second capture reagent that binds tau, wherein the first and second capture reagents are on a surface, and the surface further comprises an anchoring reagent; (iii) a first detection reagent that binds tau, wherein the first detection reagent comprises a first nucleic acid probe; and (iv) a second detection reagent that binds tau, wherein the second detection reagent comprises a second nucleic acid probe, thereby forming a complex on the surface comprising the first and second capture reagents, tau, and the first and second detection reagents; (b) using an extension process that requires the first and second nucleic acid probes to be in proximity, extending the second nucleic acid probe to form an extended sequence comprising an anchoring region that binds to the anchoring reagent; (b) binding the extended sequence to the anchoring reagent; and (c) measuring the amount of extended sequence bound to the surface, thereby quantifying the amount of t-tau. In embodiments, the first and second capture reagents and the first and second detection reagents are capable of binding to phosphorylated and non-phosphorylated tau.

In embodiments, a method of quantifying the amount of t-tau in a biological sample comprises: (a) contacting the biological sample with: (i) a first capture reagent that binds tau; (ii) a second capture reagent that binds tau, wherein the first and second capture reagents are on a surface, and the surface further comprises an anchoring reagent; (iii) a detection reagent that binds tau, wherein the detection reagent comprises a nucleic acid probe, thereby forming a complex on the surface comprising the first and second capture reagents, tau, and the detection reagent; (b) extending the nucleic acid probe to form an extended sequence comprising an anchoring region that binds to the anchoring reagent; (c) binding the extended sequence to the anchoring reagent; and (d) measuring the amount of extended sequence bound to the surface, thereby quantifying the amount of t-tau. In embodiments, the first and second capture reagents and the detection reagent are capable of binding to phosphorylated and non-phosphorylated tau.

In embodiments, a method of quantifying the amount of t-tau in a biological sample comprises: (a) contacting the biological sample with: (i) a first capture reagent that binds tau; (ii) a second capture reagent that binds tau, wherein the first and second capture reagents are on a surface; (iii) a detection reagent that binds tau, wherein the detection reagent comprises a detectable label, thereby forming a complex on the surface comprising the first and second capture reagents, tau, and the detection reagent; and measuring the amount of detectable label on the surface, thereby quantifying the amount of t-tau. In embodiments, the first and second capture reagents and the detection reagent are capable of binding to phosphorylated and non-phosphorylated tau.

In embodiments, the method further comprises providing a treatment for a blast-related brain injury. In embodiments, the treatment comprises surgical treatment, e.g., to remove dotted blood, repair skull fracture, and/or relieve pressure in the skull. In embodiments, the treatment comprises administering a medication, e.g., anti-anxiety medication, anticoagulant, anticonvulsant, antidepressant, muscle relaxant, diuretic, and/or stimulant. In embodiments, the treatment comprises rehabilitation therapy, e.g., physical therapy, occupational therapy, speech therapy, counseling, and/or cognitive therapy. In embodiments, the method of quantifying tau, e.g., p-tau or t-tau as described herein is performed before, during and after the treatment for blast-related brain injury. In embodiments, the blast-related brain injury comprises concussive injury, subconcussive injury, acute concussive injury, impact head injury, acceleration or deceleration head trauma, closed-skull neurotrauma, traumatic brain injury, stroke, seizure, status epilepticus, chronic traumatic encephalopathy (CTE), a neurodegenerative disease, or a combination thereof.

Kits

In embodiments, the invention provides a kit for detecting phosphorylated tau (p-tau) in a biological sample comprising, in one or more vials, containers, or compartments: (a) optionally, a surface; (b) a first capture reagent that binds non-phosphorylated tau; (c) a second capture reagent that binds non-phosphorylated tau; (d) a first detection reagent that binds non-phosphorylated tau; and (e) a second detection reagent that binds p-tau. In embodiments, the kit does not comprise a surface. In embodiments, the kit comprises a surface. In embodiments, the kit does not comprise a surface.

In embodiments, the invention provides a kit for detecting phosphorylated tau (p-tau) in a biological sample comprising, in one or more vials, containers, or compartments: (a) optionally, a surface; (b) a first capture reagent that binds non-phosphorylated tau; (c) a second capture reagent that binds non-phosphorylated tau; and (d) a detection reagent that binds p-tau. In embodiments, the kit comprises a surface. In embodiments, the kit does not comprise a surface.

In embodiments, the invention provides a kit for detecting total tau (t-tau) in a biological sample comprising, in one or more vials, containers, or compartments: (a) optionally, a surface; (b) a first capture reagent that binds tau and that is immobilized to or capable of being immobilized to the surface; (c) a second capture reagent that binds tau and that is immobilized to or capable of being immobilized to the surface; (d) a first detection reagent that binds tau and that comprises a first nucleic acid probe or is capable of being conjugated to a first nucleic acid probe; and (e) a second detection reagent that binds tau and that comprises a second nucleic acid probe or is capable of being conjugated to a second nucleic acid probe. In embodiments, the kit comprises a surface. In embodiments, the kit does not comprise a surface.

In embodiments, the invention provides a kit for detecting total tau (t-tau) in a biological sample comprising, in one or more vials, containers, or compartments: (a) optionally, a surface; (b) a first capture reagent that binds tau and that is immobilized to or capable of being immobilized to the surface; (c) a second capture reagent that binds tau and that is immobilized to or capable of being immobilized to the surface; and (d) a detection reagent that binds tau and that comprises a nucleic acid probe or a detectable label, or that is capable of being conjugated to a nucleic acid probe or a detectable label. In embodiments, the kit comprises a surface. In embodiments, the kit does not comprise a surface.

Capture reagents are described herein. In embodiments, the first capture reagent is an antibody, antigen, ligand, receptor, oligonucleotide, hapten, epitope, mimotope, or an aptamer. In embodiments, the first capture reagent is an antibody or a variant thereof, including an antigen/epitope-binding portion thereof, an antibody fragment or derivative, an antibody analogue, an engineered antibody, or a substance that binds to antigens in a similar manner to antibodies. In embodiments, the first capture reagent comprises at least one heavy or light chain complementarity determining region (CDR) of an antibody. In embodiments, the first capture reagent comprises at least two CDRs from one or more antibodies. In embodiments, the first capture reagent is an antibody or antigen-binding fragment thereof.

In embodiments, the first capture reagent is capable of binding to non-phosphorylated tau. In embodiments, the first capture reagent is capable of binding to p-tau. In embodiments, the first capture reagent is capable of binding to non-phosphorylated tau and p-tau. In embodiments, the first capture reagent is capable of binding to p-tau that is phosphorylated at T175, T181, T212, 5214, cis T231, trans T231, 5293, 5396, 5610, or a combination thereof.

In embodiments, the second capture reagent is an antibody, antigen, ligand, receptor, oligonucleotide, hapten, epitope, mimotope, or an aptamer. In embodiments, the second capture reagent is an antibody or a variant thereof, including an antigen/epitope-binding portion thereof, an antibody fragment or derivative, an antibody analogue, an engineered antibody, or a substance that binds to antigens in a similar manner to antibodies. In embodiments, the second capture reagent comprises at least one heavy or light chain complementarity determining region (CDR) of an antibody. In embodiments, the second capture reagent comprises at least two CDRs from one or more antibodies. In embodiments, the second capture reagent is an antibody or antigen-binding fragment thereof.

In embodiments, the second capture reagent is capable of binding to non-phosphorylated tau. In embodiments, the second capture reagent is capable of binding to p-tau. In embodiments, the second capture reagent is capable of binding to non-phosphorylated tau and p-tau. In embodiments, the second capture reagent is capable of binding to p-tau that is phosphorylated at T175, T181, T212, 5214, cis T231, trans T231, S293, S396, 5610, or a combination thereof.

In embodiments, each of the first and second capture reagents is an antibody or antigen-binding fragment thereof. In embodiments, each of the first and second capture reagents binds to non-phosphorylated tau. In embodiments, each of the first and second capture reagents that bind non-phosphorylated tau is capable of binding p-tau. In embodiments, each of the first and second capture reagents is capable of binding to p-tau is phosphorylated at T175, T181, T212, 5214, cis T231, trans T231, S293, S396, 5610, or a combination thereof. In embodiments, the first and second capture reagents are the antibodies MSD clone AA-26-VEC0983-0981 and MSD clone AA-25-VEC0728-0727 (Meso Scale Diagnostics, Rockville, MD, USA, "MSD").

Detection reagents are described herein. In embodiments comprising first and second detection reagents, the first detection reagent is an antibody, antigen, ligand, receptor, oligonucleotide, hapten, epitope, mimotope, or an aptamer. In embodiments, the first detection reagent is an antibody or a variant thereof, including an antigen/epitope-binding portion thereof, an antibody fragment or derivative, an antibody analogue, an engineered antibody, or a substance that binds to antigens in a similar manner to antibodies. In embodiments, the first detection reagent comprises at least one heavy or light chain complementarity determining region (CDR) of an antibody. In embodiments, the first detection reagent comprises at least two CDRs from one or more antibodies. In embodiments, the first detection reagent is an antibody or antigen-binding fragment thereof.

In embodiments comprising first and second detection reagents, the first detection reagent is capable of binding to non-phosphorylated tau. In embodiments, the first detection reagent is capable of binding to p-tau. In embodiments, the first detection reagent binds to non-phosphorylated tau and p-tau. In embodiments, the first detection reagent is capable of binding to p-tau that is phosphorylated at T175, T181, T212, 5214, cis T231, trans T231, 5293, 5396, S610, or a combination thereof.

In embodiments comprising first and second detection reagents, the second detection reagent is an antibody, antigen, ligand, receptor, oligonucleotide, hapten, epitope, mimotope, or an aptamer. In embodiments, the second detection reagent is an antibody or a variant thereof, including an antigen/epitope-binding portion thereof, an antibody fragment or derivative, an antibody analogue, an engineered antibody, or a substance that binds to antigens in a similar manner to antibodies. In embodiments, the second detection reagent comprises at least one heavy or light chain complementarity determining region (CDR) of an antibody. In embodiments, the second detection reagent comprises at least two CDRs from one or more antibodies. In embodiments, the second detection reagent is an antibody or antigen-binding fragment thereof.

In embodiments where the kit is for detecting p-tau and comprises first and second detection reagents, the second detection reagent binds to p-tau. In embodiments, the second detection reagent is capable of binding to p-tau that is phosphorylated at T175, T181, T212, S214, cis T231, trans T231, S293, S396, 5610, or a combination thereof. In embodiments where the kit is for detecting p-tau, the second detection reagent does not bind non-phosphorylated tau.

In embodiments where the kit is for detecting t-tau and comprises first and second detection reagents, the second reagent is capable of binding to non-phosphorylated tau. In embodiments, the second detection reagent is capable of binding to p-tau. In embodiments, the second detection reagent binds to non-phosphorylated tau and p-tau. In embodiments, the second detection reagent is capable of binding to p-tau that is phosphorylated at T175, T181, T212, S214, cis T231, trans T231, S293, S396, 5610, or a combination thereof.

In embodiments, the first detection reagent of the kit comprises a first nucleic acid probe. In embodiments, the second detection reagent of the kit comprises a second nucleic acid probe. In embodiments, the kit comprises first and second detection reagents that do not comprise nucleic acid probes, and the kit further comprises a first nucleic acid probe, a second nucleic acid probe, and a reagent for conjugating: the first nucleic acid probe to the first detection reagent, and the second nucleic acid probe to the second detection reagent. In embodiments, the reagent comprises a first reactive group that reacts with the first or second detection reagent, and a second reactive group that reacts with the first or second nucleic acid probe. In embodiments, the first and second reactive groups are substantially non-reactive with each other. In embodiments, the kit comprises a first reagent for conjugating the first detection reagent to the first nucleic acid probe, and a second reagent for conjugating the second detection reagent to the second nucleic acid probe. Examples of reactive groups and their reaction partners (e.g., on the nucleic acid probe or the detection reagent) include, but are not limited to, amine and N-hydroxysuccinimide (NHS) ester; thiol and maleimide; thiol and iodoacetamide; thiol and activated disulfide; alkene or strained alkene and tetrazine; alkyne or strained alkyne and azide; and the like. Conjugation of nucleic acid probes to detection reagents is further described in, e.g., WO 2020/180645.

In embodiments, the kit comprises a plurality of capture reagents and/or detection reagents (e.g., a plurality of first and second capture reagents and a plurality of first and second detection reagents as described herein) for a multiplexed method that quantifies the amount of non-phosphorylated tau and/or p-tau that is phosphorylated at one or more of T175, T181, T212, S214, cis T231, trans T231, 5293, 5396, and 5610, as described herein. In embodiments, the kit comprises a first capture reagent that binds non-phosphorylated tau, a second capture reagent that binds non-phosphorylated tau, a first detection reagent that binds non-phosphorylated tau, and a plurality of second detection reagents, wherein the plurality of second detection reagents comprises: a second detection reagent that binds non-phosphorylated tau, a second detection reagent that binds pT175-tau, a second detection reagent that binds pT181-tau, a second detection reagent that binds pT212-tau, a second detection reagent that binds pS214-tau, a second detection reagent that binds pcisT231-tau, a second detection reagent that binds ptransT231-tau, a second detection reagent that binds pS293-tau, a second detection reagent that binds pS396-tau, and/or a second detection reagent that binds pS610-tau.

In embodiments comprising a detection reagent, the detection reagent is an antibody, antigen, ligand, receptor, oligonucleotide, hapten, epitope, mimotope, or an aptamer. In embodiments, the detection reagent is an antibody or a variant thereof, including an antigen/epitope-binding portion thereof, an antibody fragment or derivative, an antibody analogue, an engineered antibody, or a substance that binds to antigens in a similar manner to antibodies. In embodiments, the detection reagent comprises at least one heavy or light chain complementarity determining region (CDR) of an antibody. In embodiments, the detection reagent comprises at least two CDRs from one or more antibodies. In embodiments, the detection reagent is an antibody or antigen-binding fragment thereof.

In embodiments where the kit is for detecting p-tau and comprises a detection reagent, the detection reagent binds to p-tau. In embodiments, the detection reagent is capable of binding to p-tau that is phosphorylated at T175, T181, T212, 5214, cis T231, trans T231, 5293, 5396, S610, or a combination thereof. In embodiments where the kit is for detecting p-tau, the detection reagent does not bind non-phosphorylated tau. In embodiments, the detection reagent is the antibody MSD clone AA-114-VEC1367-1366. In embodiments, the detection reagent that binds to p-tau that is phosphorylated at T175 is the antibody MSD clone 4608-C46-1. In embodiments, the detection reagent that binds to p-tau that is phosphorylated at cis T231 is the antibody MSD clone 4644-J87-1.

In embodiments where the kit is for detecting t-tau and comprises a detection reagent, the detection reagent is capable of binding to non-phosphorylated tau. In embodiments, the detection reagent is capable of binding to p-tau. In embodiments, the detection reagent binds to non-phosphorylated tau and p-tau. In embodiments, the detection reagent is capable of binding to p-tau that is phosphorylated at T175, T181, T212, 5214, cis T231, trans T231, S293, S396, S610, or a combination thereof. In embodiments, the detection reagent is the antibody MSD clone AA-114-VEC1367-1366. In embodiments, the detection reagent that binds to p-tau that is phosphorylated at T175 is the antibody MSD clone 4608-C46-1. In embodiments, the detection reagent that binds to p-tau that is phosphorylated at cis T231 is the antibody MSD clone 4644-J87-1.

In embodiments, the detection reagent of the kit comprises a nucleic acid probe. In embodiments, the kit comprises a detection reagent that does not comprise nucleic acid probes, and the kit further comprises a nucleic acid probe and a reagent for conjugating the nucleic acid probe to the detection reagent. In embodiments, the reagent comprises a first reactive group that reacts with the detection reagent, and a second reactive group that reacts with the nucleic acid probe. In embodiments, the first and second reactive groups are substantially non-reactive with each other. Conjugation of detection reagents and nucleic acid probes is described herein.

In embodiments, the kit comprises a plurality of capture reagents and/or detection reagents (e.g., a plurality of first and second capture reagents and a plurality of detection reagents as described herein) for a multiplexed method that quantifies the amount of non-phosphorylated tau and/or p-tau that is phosphorylated at one or more of T175, T181, T212, S214, cis T231, trans T231, S293, S396, and 5610, as described herein. In embodiments, the kit comprises a first capture reagent that binds non-phosphorylated tau, a second capture reagent that binds non-phosphorylated tau, and a plurality of detection reagents, wherein the plurality of detection reagents comprises: a detection reagent that binds non-phosphorylated tau, a detection reagent that binds pT175-tau, a detection reagent that binds pT181-tau, a detection reagent that binds pT212-tau, a detection reagent that binds pS214-tau, a detection reagent that binds pcisT231-tau, a detection reagent that binds ptransT231-tau, a detection reagent that binds pS293-tau, a detection reagent that binds pS396-tau, and/or a detection reagent that binds pS610-tau.

In embodiments, the detection reagent of the kit comprises a detectable label. In embodiments, the kit comprises a detection reagent that does not comprise a detectable label, and the kit further comprises a reagent for conjugating the detectable label to the detection reagent. In embodiments, the reagent comprises a first reactive group that reacts with the detection reagent, and a second reactive group that reacts with the detectable label. In embodiments, the first and second reactive groups are substantially non-reactive with each other. Conjugation of detection reagents with detectable labels can be performed in a similar manner with similar reagents for conjugating detection reagents with nucleic acid probes, as described herein.

Detectable labels are described herein. In embodiments, the detectable label is capable of being measured by light scattering, optical absorbance, fluorescence, chemiluminescence, electrochemiluminescence (ECL), bioluminescence, phosphorescence, radioactivity, magnetic field, or combinations thereof. In embodiments, the detectable label comprises an ECL label. In embodiments, the detectable label comprises multiple ECL labels. In embodiments, the detectable label comprises ruthenium.

In embodiments, the kit further comprises an anchoring reagent. Anchoring reagents are described herein. In embodiments, the anchoring reagent comprises an oligonucleotide, aptamer, aptamer ligand, antibody, antigen, ligand, receptor, hapten, epitope, or a mimotope. In embodiments, the anchoring reagent comprises a single stranded oligonucleotide. In embodiments, the anchoring reagent comprises a double stranded oligonucleotide.

In embodiments comprising nucleic acid probes, the kit further comprises a labeled probe comprising a detection oligonucleotide and a detectable label. Labeled probes and detectable labels are described herein.

In embodiments, the surface comprises a particle. In embodiments, the surface comprises a well of multi-well plate. In embodiments, the surface comprises a plurality of distinct binding domains. In embodiments, the surface comprises an electrode. In embodiments, the electrode is a carbon ink electrode.

In embodiments, the first and second capture reagents are provided in the kit as immobilized on the surface. In embodiments comprising an anchoring reagent, the anchoring reagent is provided in the kit as immobilized on the surface. In embodiments, the first and second capture reagents and/or the anchoring reagent are directly immobilized on the surface. In embodiments, the first and second capture reagents and/or the anchoring reagent are indirectly immobilized on the surface via secondary binding reagents, e.g., a targeting agent. In embodiments, the first and second capture reagents are not provided in the kit as immobilized on the surface. In embodiments, the kit further comprises a reagent for immobilizing the first and second capture reagents to the surface. In embodiments comprising an anchoring reagent, the anchoring reagent is not provided in the kit as immobilized on the surface. In embodiments, the kit further comprises a reagent for immobilizing the anchoring reagent to the surface. Methods and reagents for immobilizing capture reagents and/or anchoring reagents to surfaces, e.g., via targeting agents, targeting agent complements, and bridging agents are described herein.

In embodiments, the kit further comprises a template oligonucleotide. Template oligonucleotides, e.g., for performing the polymerase chain reaction (PCR), ligase chain reaction (LCR), strand displacement amplification (SDA), self-sustained synthetic reaction (3SR), and/or isothermal amplification (such as, e.g., helicase-dependent amplification or rolling circle amplification), are described herein. In embodiments comprising first and second detection reagents, the template oligonucleotide is capable of binding to the first and second nucleic acid probes. In embodiments comprising a detection reagent, the template oligonucleotide is capable of binding to the nucleic acid probe.

In embodiments, one or more components of the kit is lyophilized. In embodiments comprising first and second detection reagents, the first capture reagent, the second capture reagent, the first detection reagent, and/or the second detection reagent is lyophilized. In embodiments, the first capture reagent, the second capture reagent, the first detection reagent, and/or the second detection reagent is provided in solution.

In embodiments comprising a detection reagent, the first capture reagent, the second capture reagent, and/or second detection reagent is lyophilized. In embodiments, the first capture reagent, the second capture reagent, and/or the detection reagent is provided in solution.

In embodiments, the capture and detection reagents and other components in the kit are provided separately. In embodiments, the components of the kit are provided separately according to each component's optimal shipping and/or storage conditions.

In embodiments, the kit further comprises a polymerase, a ligase, a buffer, a blocking agent, a co-reactant, a diluent, a stabilizing agent, a calibration agent, an assay consumable, an electrode, or a combination thereof.

In embodiments, the kit further comprises a calibration reagent. In embodiments, the calibration reagent comprises a known quantity of non-phosphorylated tau or p-tau. In embodiments, the kit comprises multiple calibration reagents comprising a range of concentrations of non-phosphorylated tau or p-tau. In embodiments, the multiple calibration reagents comprise concentrations of non-phosphorylated tau or p-tau near the upper and lower limits of quantitation for the method. In embodiments, the multiple calibration reagents span the entire dynamic range of the method. In embodiments, the calibration reagent is a positive control reagent. In embodiments, the calibration reagent is a negative control reagent. In embodiments, the positive or negative control reagent is used to provide a basis of comparison for the biological sample to be tested with the methods of the present invention. In embodiments, the calibration reagent is lyophilized. In embodiments, the calibration reagent is provided in solution.

In embodiments, the kit further comprises a polymerase, e.g., for performing polymerase chain reaction (PCR), ligase chain reaction (LCR), strand displacement amplification (SDA), self-sustained synthetic reaction (3SR), and/or isothermal amplification (such as, e.g., helicase-dependent amplification or rolling circle amplification). In embodiments, the kit further comprises a ligase, e.g., for ligating the template oligonucleotide.

In embodiments, the kit further comprises a buffer, e.g., an assay buffer, a reconstitution buffer, a storage buffer, a read buffer, or a combination thereof. In embodiments, the kit further comprises a co-reactant, e.g., for performing an electrochemiluminescence measurement. Exemplary co-reactants are described, e.g., in WO 2020/142313.

In embodiments, the kit further comprises a blocking agent, e.g., to decrease non-specific binding by components other than tau to the capture and detection reagents described herein. Exemplary blocking agents include, but are not limited to, mBSA, sheared poly(A), polyBSA-I, mIgG, Tween, polyBSA-II, yeast RNA, mBSA+poly(a), and/or polyBSA+poly(A). In embodiments, the kit further comprises a diluent for one or more components of the kit. In embodiments, a kit comprising the components above includes stock concentrations of the components that are 5×, 10×, 20×, 30×, 40×, 50×, 60×, 70×, 80×, 90×, 100×, 125×, 150× or higher fold concentrations of a working concentration for the methods provided herein. In embodiments, the kit further comprises a stabilizing agent, e.g., for storage of one or more components of the kit.

In embodiments, the kit further comprises an assay consumable, e.g., assay modules, vials, tubes, liquid handling and transfer devices such as pipette tips, covers and seals, racks, labels, and the like. In embodiments, the kit further comprises an electrode, e.g., for performing an electrochemiluminescence measurement. In embodiments, the electrode is applied to the surface provided herein. In embodiments, the kit further comprises an assay instrument and/or instructions for carrying out the methods described herein.

All references cited herein, including patents, patent applications, papers, textbooks and the like, and the references cited therein, to the extent that they are not already, are hereby incorporated herein by reference in their entirety.

| SEQUENCES |
| --- |
| SEQ ID NO: 1 |
| amino acid sequence of human tau protein |
| MAEPRQEFEV MEDHAGTYGL GDRKDQGGYT MHQDQEGDTD |
| AGLKESPLQT PTEDGSEEPG SETSDAKSTP TAEDVTAPLV |
| DEGAPGKQAA AQPHTEIPEG TTAEEAGIGD TPSLEDEAAG |
| HVTQARMVSK SKDGTGSDDK KAKGADGKTK IATPRGAAPP |
| GQKGQANATR IPAKTPPAPK TPPSSGEPPK SGDRSGYSSP |
| GSPGTPGSRS RTPSLPTPPT REPKKVAVVR TPPKSPSSAK |
| SRLQTAPVPM PDLKNVKSKI GSTENLKHQP GGGKVQIINK |
| KLDLSNVQSK CGSKDNIKHV PGGGSVQIVY KPVDLSKVTS |

| -continued |
| --- |
| SEQUENCES |
| KCGSLGNIHH KPGGGQVEVK SEKLDFKDRV QSKIGSLDNI |
| THVPGGGNKK IETHKLTFRE NAKAKTDHGA EIVYKSPVVS |
| GDTSPRHLSN VSSTGSIDMV DSPQLATLAD EVSASLAKQG |
| L |

EXAMPLES

Example 1. Screen for Biomarkers of Chronic Traumatic Brain Injury Symptoms

A screen for biomarkers was conducted using an immunoassay panel of 68 biomarkers associated with four key traumatic brain injury (TBI) pathways, shown in FIG. 1. The biomarkers in bold in FIG. 1 indicate the 53 assays that have been analyzed with an available sample.

The screen was conducted using serum obtained for 137 veterans enrolled in a study of chronic TBI at a Veterans Administration (VA) Hospital ("Clinical and Neuroimaging Correlates of Neurodegeneration in Military mTBI," CENC Study 49; PI=Nicholas Davenport, University of Minnesota, VA. Subjects were enrolled military members and veterans with history of combat deployment, who sustained lifetime mild TBI (mTBI) as well as controls, i.e., combat deployed with no lifetime TBI).

Ordinal logistic regression was performed to assess correlation between biomarker values and number of blast TBIs (ranging from zero to three). P-tau levels were normalized to total tau levels (e.g., S396 ratio=pS396-tau/tau) to compensate for the cross-reactivity of p-tau assays with non-phosphorylated tau. Biomarker data were log-transformed (base 10), and log normality was confirmed by a QQ plot. The analysis package computed Odds Ratio (OR) and associated p-value. The OR quantitates the increase in likelihood for another blast TBI for a 10× increase in biomarker level.

Results are shown in FIGS. 2A and 2B. As shown in FIG. 2A, the top biomarkers most closely associated with blast exposure were phosphorylated tau (S396, cis T231, S293, 5214, T175). The results for p-tau are shown in Table 1. P-tau levels were normalized to total tau levels to compensate for cross-reactivity of p-tau assays with non-phosphorylated tau.

TABLE 1

| Biomarker | Odds Ratio (p-value) | Odds Ratio for p-tau levels normalized to total tau levels (p-value) |
| --- | --- | --- |
| T175 | 3.4 (0.03) | 3.7 (0.03) |
| T181 | 3.3 (0.11) | 3.6 (0.11) |
| S214 | 9.5 (0.02) | 4.7 (0.07) |
| cis T231 | 5.0 (0.02) | 9.6 (0.005) |
| trans T231 | 5.5 (0.09) | 2.8 (0.29) |
| S293 | 7.2 (0.006) | 6.1 (0.01) |
| S396 | 4.9 (0.01) | 10.4 (0.005) |
| Tau | 1.2 (0.83) | |

FIG. 2B shows the results of ECL-based immunoassays for tau phosphorylated at different sites (T175, T181, T214, cis T231, trans T231, S396, and S610), plotted against the measured ECL signal from an immunoassay for total tau. Each circle represents a serum sample. Dashed lines indicate the labeled percentage of total tau signal. Four samples were noted to have consistently high levels of p-tau T175, T181, cis T231, and 5610 relative to total tau. In particular, one subject had an average ECL signal of 3,414 counts for cis p-tau T231 compared to 31,593 counts for total tau. The signal for cis p-tau T231 was 11% of the total tau signal, which is significantly higher than expected from a cross-reactivity of approximately 1%. After unblinding the samples, it was determined that all four samples with high ratios of p-tau to total tau were obtained from individuals who experienced blast TBI. Since 44 of 131 samples with available data (34%) had a history of blast TBI, the likelihood that the four samples with highest level of p-tau would all have blast TBI by chance alone is 1.2%. The subject with high counts of cis p-tau T231 had one of the highest TBI exposures (2 blast TBIs and 3 non-blast TBIs), and reported post-concussive symptoms. This subject also had the highest level of Nf-L among the subjects.

Figure 3:
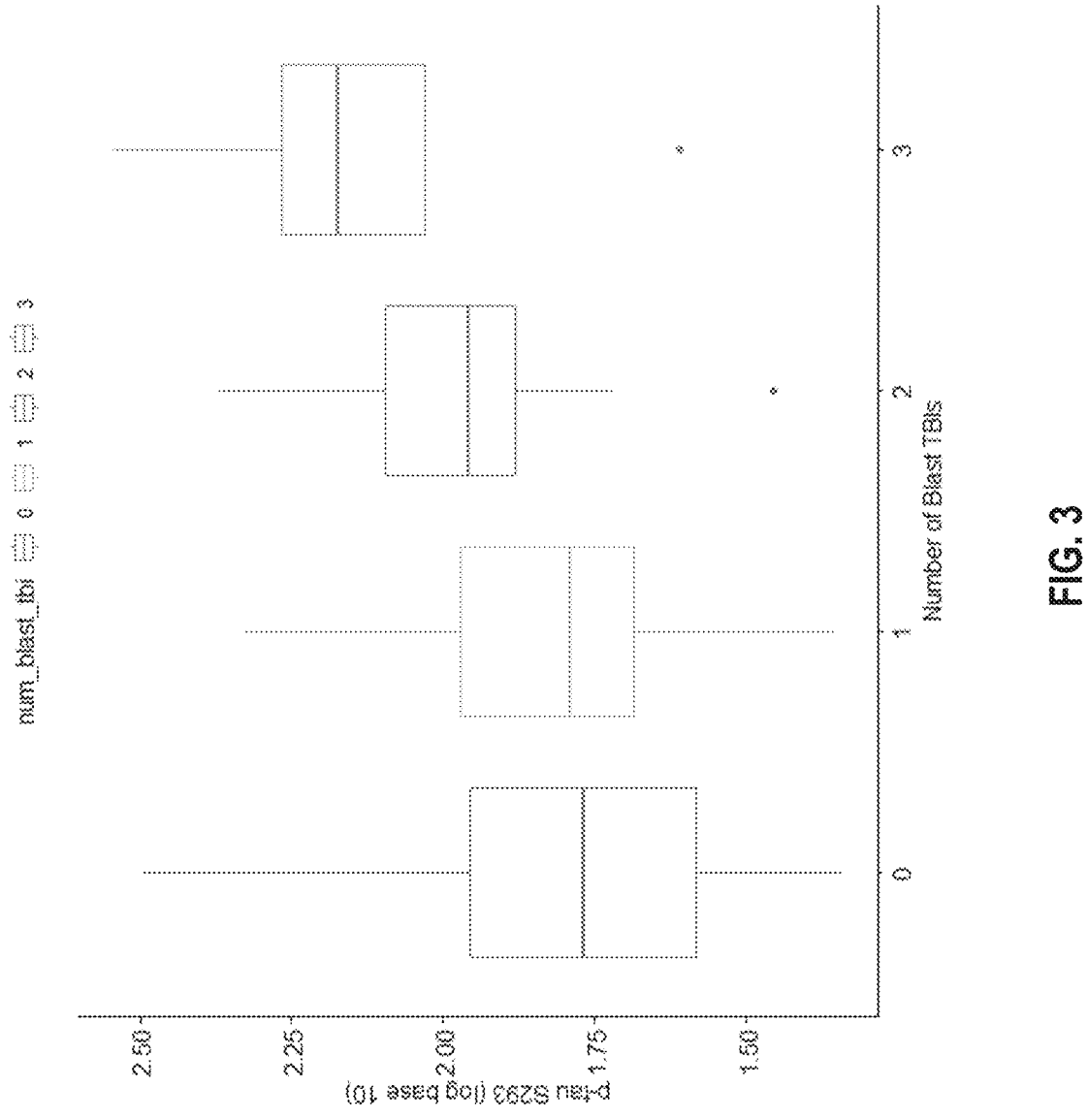

FIG. 3 shows box plots of a representative species (S293), indicating that the number of blast exposures was related to both the absolute levels of p-tau and ratio of p-tau to total tau.

Figure 5:
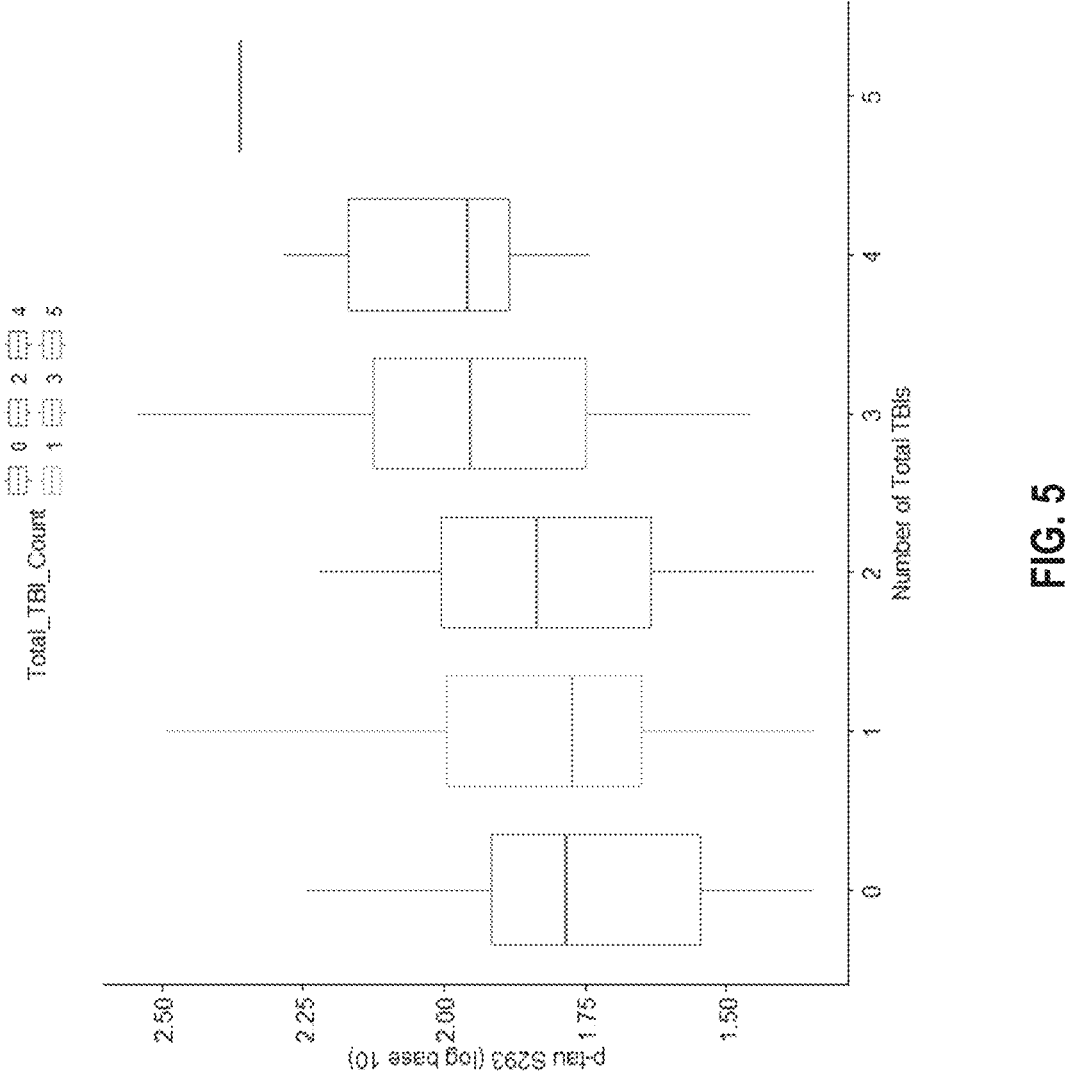

The association between p-tau levels and total number of TBIs (both from blast- and non-blast related events) was also assessed in a similar manner. Results in FIG. 4 show that the serum levels of p-tau were correlated with the total number of TBIs, but the correlations were weaker than for blast TBIs alone (see FIG. 2). FIG. 5 shows that serum levels of p-tau were not significantly correlated with the number of non-blast TBIs.

Receiver-operator curve (ROC) analysis was performed to assess the differences in biomarkers between subjects with or without repeated blast TBI (two or more blast TBIs). Results are shown in FIGS. 6A and 6B. Consistent with the regression analysis described above, p-tau levels were higher in individuals with repeated blast TBI.

Example 2. Dual-Capture Tau Immunoassay

An ultrasensitive immunoassay to measure total tau in serum and plasma was developed. The immunoassay utilized a synergistic combination of two capture antibodies, hereinafter referred to as a "dual-capture" immunoassay. The dual-capture immunoassay was tested against immunoassay formats utilizing a single capture antibody, with the following samples: plasma from healthy individuals, plasma from severe traumatic brain injury (sTBI) patients, cerebrospinal fluid (CSF) from healthy individuals, and CSF from sTBI patients, as summarized in FIG. 7.

The immunoassays were performed as follows:
1. Wash plate 3× with PBS-TWEEN.
2. Add 50 μL of coating solution to the well. (Coating solution contains 1 μg/mL of each capture antibody)
3. Incubate for one hour with shaking at 705 rpm.
4. Wash plate 3× with PBS-TWEEN.
5. Add 25 μL/well assay diluent.
6. Add 25 μL/well calibrators according to schematic in FIG. 7.
7. Incubate for one hour with shaking at 705 rpm.
8. Wash plate 3× with PBS-TWEEN.
9. Add 25 μL/well detection antibody solution. (Detection antibody solution contains 1 μg/mL of detection antibody)
10. Incubate for one hour with shaking at 705 rpm.
11. Wash plate 3× with PBS-TWEEN.
12. Add 150 μL of read buffer to each well.
13. Read plate on imager.

Figure 8B:
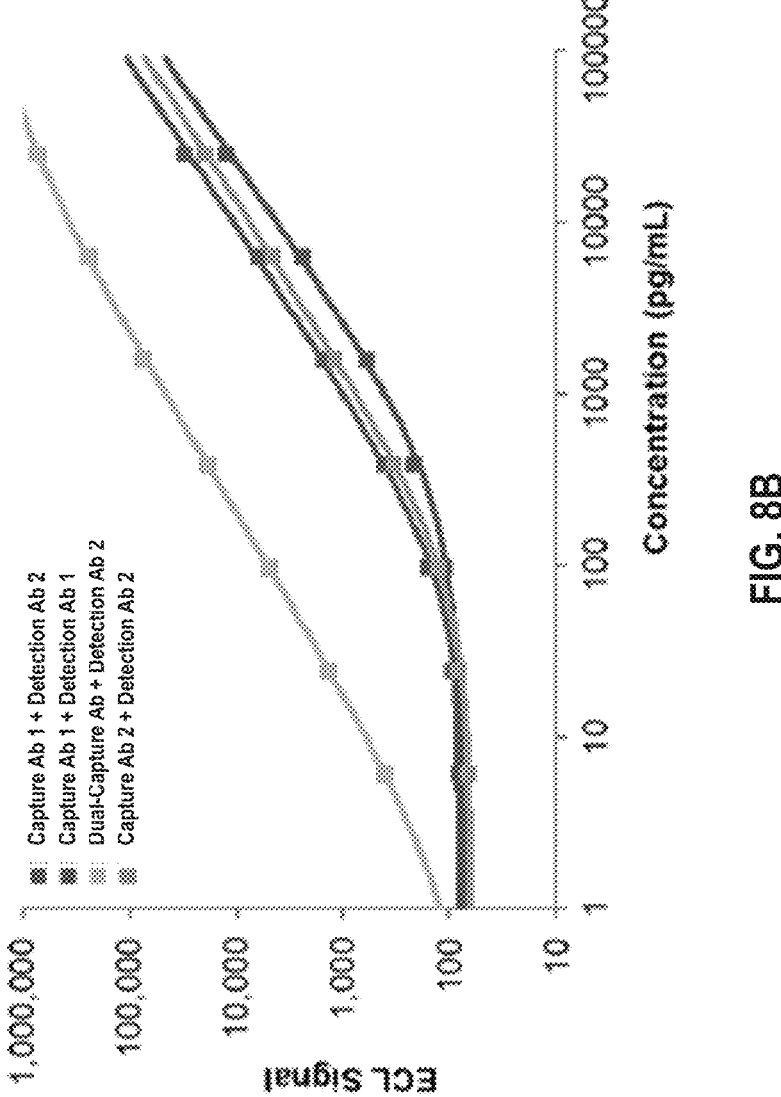

Results are shown in FIGS. 8A and 8B. The immunoassays utilizing a single capture antibody did not readily detect tau in CSF, while the dual-capture immunoassay detected tau in normal CSF, TBI CSF, and TBI plasma, as shown by the low limit of detection (LOD) of 0.4 for the dual-capture immunoassay, compared to LODs of 99, 32, and 39 for the single capture antibody immunoassays.

Example 3. Comparison of Dual-Capture Tau and Non-Dual Capture Tau Assays

A dual-capture immunoassay for measuring tau that utilizes first and second capture reagents and a detection reagent linked to a nucleic acid probe as described herein ("nucleic acid probe detection assay") was performed using recombinant antibodies. A further dual-capture immunoassay for measuring tau that utilizes first and second capture reagents and a detection reagent linked to a detectable label as described herein ("detectable label detection assay") was performed using non-recombinant antibodies. The results for the nucleic acid probe detection assay and the detectable label detection assay were highly correlated (r=0.9825), indicating that both assay formats had comparable performance. See FIG. 9A.

Figure 9B:
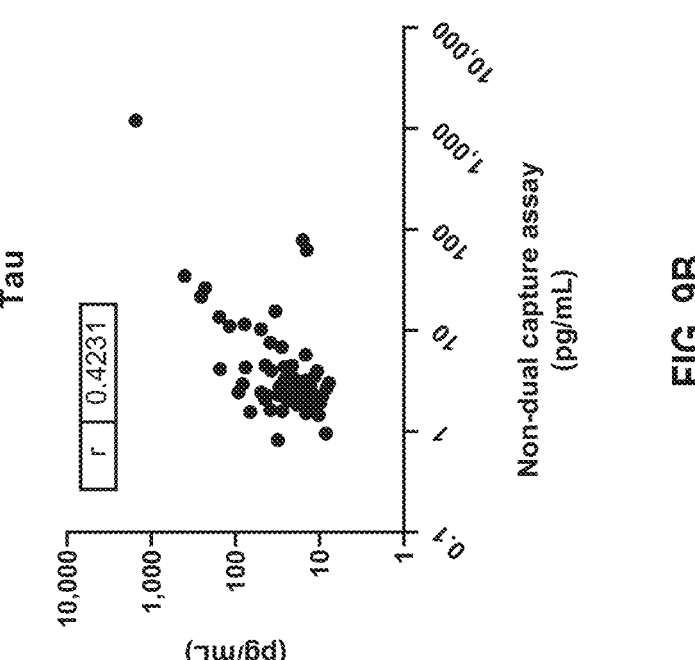
FIGS. 9A and 9B show the results of immunoassays described in Example 3.
Figure 9A:
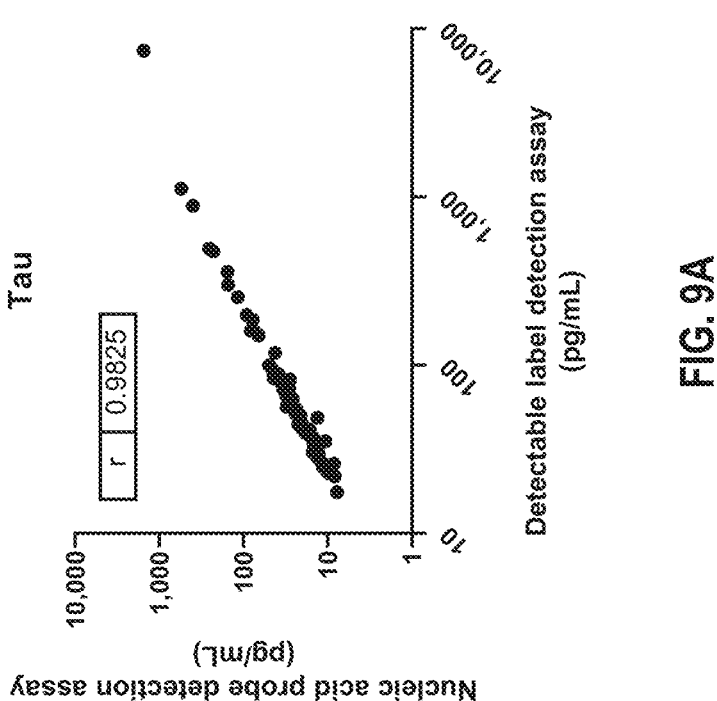

Results from the nucleic acid probe detection assay were also plotted against a non-dual capture tau assay utilizing a Single Molecule Array (SIMOA®) tau assay developed by QUANTERIX®, e.g., as described in Chen et al., *Alzheimers Dement.* 15(3):487-496 (2019) ("SIMOA assay"). As shown in FIG. 9B, the SIMOA assay did not have strong correlation with the nucleic acid probe detection assay (r=0.4231), indicating that the nucleic acid probe detection assay, which utilizes a dual-capture assay format, obtained different antibody measurements than a non-dual capture assay.

Figures 10A, 10B, 10C, 10D, 10E:
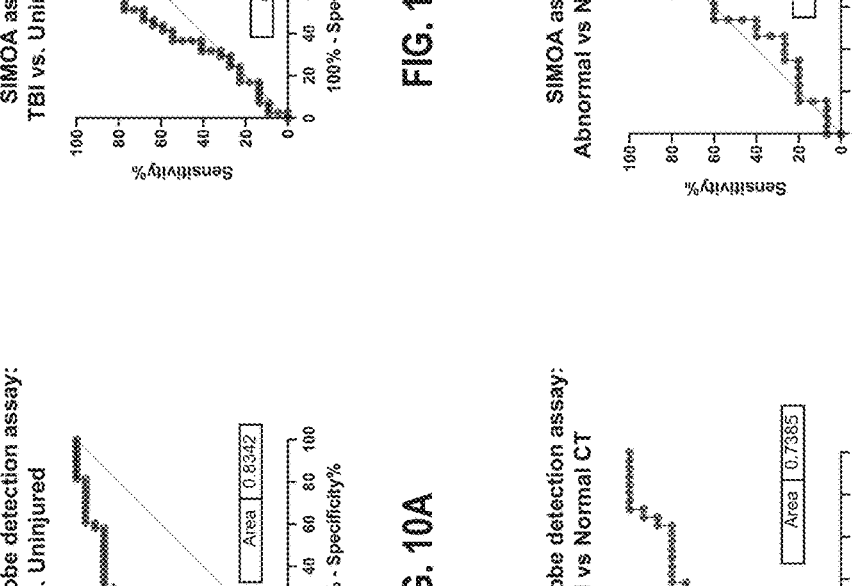
FIGS. 10A-10E show the results of immunoassays described in Example 3.

The nucleic acid probe detection assay and the SIMOA assay were also performed on: plasma samples from subjects who have traumatic brain injury (TBI) or who were uninjured (control); and from subjects who had abnormal or normal CT scan results. As shown in FIGS. 10A and 10B, the nucleic acid probe detection assay had a higher area under the curve (AUC) value than the SIMOA assay for distinguishing between the uninjured control subjects and the subjects with TBI. As shown in FIGS. 10C and 10D, the nucleic acid probe detection assay also had a higher area under the curve (AUC) value than the SIMOA assay for distinguishing between subjects who had an abnormal vs. normal CT scan. The AUC values are summarized in FIG. 10E. A higher AUC value indicates that the assay is more accurate at distinguishing between the two populations. Thus, the nucleic acid probe detection assay had better performance than the SIMOA assay for distinguishing between subjects with or without TBI and/or with an abnormal or normal CT scan.

Example 4. Analysis of Total Tau and p-Tau in Subjects with TBI

A study was performed to analyze levels of total tau and p-tau in 501 serum samples collected from veterans and military personnel with various degrees of TBI, using the dual-capture immunoassays described herein. P-tau was detected in a subset of the samples. Total tau levels in some samples significantly exceeded the normal range. Serum levels of total tau in the 98th percentile were comparable to levels reported for individuals with neurodegeneration. Total tau levels may be useful for detecting neurodegeneration after TBI.

What is claimed is:

1. A method of quantifying the amount of phosphorylated tau (p-tau) in a biological sample, wherein the method comprises:

a) contacting the biological sample with: (i) a first capture reagent that binds to non-phosphorylated tau; (ii) a second capture reagent that binds to non-phosphorylated tau, wherein the first and second capture reagents are on a surface, and the surface further comprises an anchoring reagent; (iii) a first detection reagent that binds to non-phosphorylated tau, wherein the first detection reagent comprises a first nucleic acid probe; and (iv) a second detection reagent that binds to p-tau and does not bind to non-phosphorylated tau, wherein the second detection reagent comprises a second nucleic acid probe, thereby forming a complex on the surface comprising the first and second capture reagents, p-tau, and the first and second detection reagents;

b) using an extension process that requires the first and second nucleic acid probes to be in proximity, extending the second nucleic acid probe to form an extended sequence comprising an anchoring region that binds to the anchoring reagent;

c) binding the extended sequence to the anchoring reagent; and d) measuring the amount of extended sequence bound to the surface, thereby quantifying the amount of p-tau.

2. The method of claim 1, wherein the p-tau is phosphorylated at amino acid position T175, T181, T212, S214, cis T231, trans T231, S293, S396, S610, or a combination thereof, wherein the amino acid position corresponds to SEQ ID NO:1.

3. The method of claim 1, wherein each capture reagent and detection reagent comprises an antibody or antigen-binding fragment thereof, antigen, ligand, receptor, oligonucleotide, hapten, epitope, mimotope, or an aptamer.

4. The method of claim 1, wherein the extending comprises polymerase chain reaction (PCR), ligase chain reaction (LCR), strand displacement amplification (SDA), self-sustained synthetic reaction (3SR), isothermal amplification, or combination thereof.

5. The method of claim 1, wherein the extending comprises binding the first and second nucleic acid probes to a template oligonucleotide and extending the second nucleic acid probe by PCR.

6. The method of claim 1, wherein the anchoring reagent comprises an anchoring oligonucleotide, and wherein the extended sequence comprises an anchoring oligonucleotide complement that is complementary to the anchoring oligo-nucleotide, and a detection oligonucleotide complement that is complementary to a detection oligonucleotide; and wherein the measuring comprises contacting the extended sequence with a labeled probe comprising the detection oligonucleotide and a detectable label, and measuring the amount of detectable label bound to the surface.

7. The method of claim 1, wherein the detection reagent comprises a detectable label, and wherein the detectable label is an electrochemiluminescence (ECL) label, and the measuring comprises measuring an ECL signal.

8. The method of claim 1, wherein the surface comprises a particle.

9. The method of claim 1, wherein the surface comprises an electrode, and the measuring further comprises applying a potential to the electrode and measuring electrochemiluminescence.

10. The method of claim 1, wherein the surface comprises a plurality of distinct binding domains, and the first capture reagent, the second capture reagent, and the anchoring reagent are located on two or more distinct binding domains on the surface.

11. A method of determining the number of blast exposures experienced by a subject, comprising a) conducting the method of claim 1 on a biological sample of the subject to quantify the amount of p-tau in the biological sample; and b) determining the number of blast exposures experienced by the subject based on the amount of p-tau.

12. The method of claim 1, wherein the biological sample is whole blood, blood serum plasma, cerebrospinal fluid, urine, saliva, or an extraction or purification therefrom, or dilution thereof; and/or wherein the biological sample comprises an exosome.

13. The method of claim 1, wherein the biological sample is obtained from a subject exposed to blast, at risk of exposure to blast, or suspected of having been exposed to blast.

14. The method of claim 1, wherein the extending comprises binding the first and second nucleic acid probes to a template oligonucleotide, forming a circular template oligonucleotide, and extending the second nucleic acid probe by rolling circle amplification (RCA).

15. The method of claim 1, wherein the surface comprises a well of a multi-well plate.

16. The method of claim 1, wherein the surface comprises a particle, and the method further comprises collecting the particle on an electrode, and the measuring further comprises applying a potential to the electrode and measuring electrochemiluminescence.

17. The method of claim 1, wherein the surface comprises a plurality of distinct binding domains, and the first capture reagent, the second capture reagent, and the anchoring reagent are located on the same binding domains on the surface.

18. A method of quantifying the amount of phosphorylated tau (p-tau) in a biological sample, wherein the method comprises:

a) contacting the biological sample with: (i) a first capture reagent that binds to non-phosphorylated tau; (ii) a second capture reagent that binds to non-phosphorylated tau, wherein the first and second capture reagents are on a surface, and the surface further comprises an anchoring reagent; (iii) a detection reagent that binds to p-tau and does not bind to non-phosphorylated tau, wherein the detection reagent comprises a nucleic acid probe, thereby forming a complex on the surface comprising the first and second capture reagents, p-tau, and the detection reagent;

b) extending the nucleic acid probe to form an extended sequence comprising an anchoring region that binds to the anchoring reagent;

c) binding the extended sequence to the anchoring reagent; and d) measuring the amount of extended sequence bound to the surface, thereby quantifying the amount of p-tau.

19. The method of claim 18, wherein the extending comprises binding the nucleic acid probe to a template oligonucleotide, forming a circular template oligonucleotide, and extending the nucleic acid probe by rolling circle amplification (RCA).

20. A method of quantifying the amount of phosphorylated tau (p-tau) in a biological sample, wherein the method comprises:

a) contacting the biological sample with: (i) a first capture reagent that binds to non-phosphorylated tau; (ii) a second capture reagent that binds to non-phosphorylated tau, wherein the first and second capture reagents are on a surface; (iii) a detection reagent that binds to p-tau and does not bind to non-phosphorylated tau, wherein the detection reagent comprises a detectable label, thereby forming a complex on the surface comprising the first and second capture reagents, p-tau, and the detection reagent; and b) measuring the amount of detectable label on the surface, thereby quantifying the amount of p-tau.

* * * * *